United States Patent
Modrusan

(10) Patent No.: US 6,274,316 B1
(45) Date of Patent: Aug. 14, 2001

(54) COMPOSITIONS AND METHODS FOR DETECTING VANCOMYCIN RESISTANT ENTEROCOCCI BY CYCLING PROBE REACTIONS

(75) Inventor: Zora D. Modrusan, Vancouver (CA)

(73) Assignee: ID Biomedical Corporation, Burnaby (CA)

(*) Notice: Subject to any disclaimer, the term of this patent is extended or adjusted under 35 U.S.C. 154(b) by 0 days.

(21) Appl. No.: 09/110,048

(22) Filed: Jul. 2, 1998

Related U.S. Application Data
(60) Provisional application No. 60/090,275, filed on Jun. 22, 1998, provisional application No. 60/086,022, filed on May 18, 1998, and provisional application No. 60/051,699, filed on Jul. 3, 1997.

(51) Int. Cl.[7] ............... C12Q 1/68; C12P 19/34; C07H 21/04
(52) U.S. Cl. ............ 435/6; 435/91.1; 536/23.1; 536/24.3
(58) Field of Search ............... 435/6, 99, 21, 435/91.1; 536/23.1, 24.3

(56) References Cited

U.S. PATENT DOCUMENTS

| | | | |
|---|---|---|---|
| 4,876,187 | 10/1989 | Duck et al. | 435/6 |
| 5,011,769 * | 4/1991 | Duck et al. | 435/6 |
| 5,403,711 | 4/1995 | Walder et al. | 435/6 |
| 5,660,988 | 8/1997 | Duck et al. | 435/6 |
| 5,731,146 | 3/1998 | Duck et al. | 435/6 |
| 5,770,361 * | 6/1998 | Arthur et al. | 435/6 |

FOREIGN PATENT DOCUMENTS

| | | |
|---|---|---|
| 227 976 A2 | 7/1987 | (EP). |
| 229 701 B1 | 7/1987 | (EP). |
| 2 699 537 A1 | 6/1994 | (FR). |
| WO 95/00667 | 1/1995 | (WO). |
| WO 95/14106 | 5/1995 | (WO). |
| WO 96/08582 | 3/1996 | (WO). |
| WO96/08582 * | 3/1996 | (WO). |

OTHER PUBLICATIONS

Patel et al "Multiplex PCR detection . . . " J. of Clin. Microb. vol. 35(3): 703–707, 1997.*
Arthur et al., "The vanZ gene of Tn1546 from *Enterococcus faecium* BM4147 confers resistance to teicoplanin," *Gene* 154: 87–92, 1995.
Beggs et al., "Characterization of Mycobacterium Tuberculosis Complex Direct Repeat Sequence for Use in Cycling Probe Reaction," *Journal of Clinical Microbiology* 34(12): 2985–2989, 1996.

(List continued on next page.)

*Primary Examiner*—W. Gary Jones
*Assistant Examiner*—Jehanne Souaya
(74) *Attorney, Agent, or Firm*—Seed Intellectual Property Law Group PLLC

(57) ABSTRACT

A method for determining the presence of vancomycin antibiotic resistant gene of enterococci in a biological sample, comprising the steps of (a) treating cells contained within the biological sample to expose single stranded-target nucleic acid molecules; (b) reacting the target single-stranded cellular nucleic acids with probe(s) nucleic acid sequence complementary to a portion of the antibiotic vancomycin resistant gene and the probe having a scissile linkage, and with an enzyme molecule, under conditions, which allow the target and probe to hybridize to each other and form a double-stranded, target-probe complex, the enzyme molecule being capable of cleaving the scissile link of the target-probe complex such that one or more fragments of the nucleic acid probe is released from said complex; and (c) determining whether cleaved portions of the nucleic acid probe are produced, and thereby detecting the presence of a vancomycin antibiotic resistant gene.

17 Claims, 7 Drawing Sheets

OTHER PUBLICATIONS

Patel et al., "Multiplex PCR detection of vanA, vanB, vanC-1, and vanC-2/3 Genes in Enterococci," *Journal of Clinical Microbiology* 35(3): 703–707, 1997.

Al–Obeid et al., "Comparison of vancomycin–inducible proteins from four strains of Enterocci," *FEMS Microbiology Letters* 70: 101–106, 1990.

Brisson–Noël et al., "Cloning and Heterospecific Expression of the Resistance Determinant vanA Encoding High–Level Resistance to Glycopeptides in *Enterococcus faecium* BM4147," *Antimicrobial Agents And Chemotherapy* 34(5): 924–927, 1990.

Bugg et al., "Identification of Vancomycin Resistance Protein VanA as a D–Alanine:D–Alanine Ligase of Altered Substrate Specificity," *Biochemistry* 30: 2017–2021, 1991.

Dutka–Malen et al., "The VANA glycopeptide resistance protein is related to D–alanyl–D–alanine ligase cell wall biosynthesis enzymes," *Mol. Gen. Genet.* 224: 364–372, 1990.

Dutka–Malen et al., "Phenotypic and Genotypic Heterogeneity of Glycopeptide Resistance Determinants in Gram–Positive Bacteria," *Antimicrobial Agents And Chemotherapy* 34(10): 1875–1879, 1990.

Dutka–Malen et al., "Sequence of the vanC gene of *Enterococcus gallinarum* BM4174 encoding a D–alanine:D–alanine ligase–related protein necessary for vancomycin resistance," *Gene* 112: 53–58, 1992.

Evers et al., "The vanB gene of vancomycin–resistant *Enterococcus faecalis* V583 is structurally related to genes encoding D–Ala:D–Ala ligases and glycopeptide–resistance proteins VanA and VanC," *Gene* 124: 143–144, 1993.

Leclercq et al., "Transferable Vancomycin and Teicoplanin Resistance in *Enterococcus faecium,*" *Antimicrobial Agents And Chemotherapy* 33(1): 10–15, 1989.

Sahm et al., "In Vitro Susceptibility Studies of Vancomycin–Resistant *Enterococcus faecalis,*" *Antimicrobial Agents And Chemotherapy* 33(9): 1588–1591, 1989.

* cited by examiner

SEQUENCE LISTING

<160> NUMBER OF SEQ ID NOS: 32

<210> SEQ ID NO: 1
<211> LENGTH: 27
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 1
ttaataaccc aaaaggcggg agtagct                                             27

<210> SEQ ID NO: 2
<211> LENGTH: 27
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 2
agctactccc gccttttggg ttattaa                                             27

<210> SEQ ID NO: 3
<211> LENGTH: 27
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 3
tacattctta caaaaaatgc gggcatc                                             27

<210> SEQ ID NO: 4
<211> LENGTH: 27
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 4
gatgcccgca tttttgtaa gaatgta                                              27

<210> SEQ ID NO: 5
<211> LENGTH: 27
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 5
gccgatagtc tccccgccat attctcc                                             27

<210> SEQ ID NO: 6
<211> LENGTH: 27
<212> TYPE: DNA
<213> ORGANISM: Artificial Sequence
<220> FEATURE:
<223> OTHER INFORMATION: Description of Artificial Sequence: Solid Phase
    Synthesis of Nucleic Acid Probes Complementary to
    VRE genes vanA, vanB, vanB2, vanC1, vanC2, vanC3,
    vanD, or variants thereof

<400> SEQUENCE: 6
ggagaatatg cgggagac tatcggc                                    27

<210> SEQ ID NO: 7
<211> LENGTH: 20
<212> TYPE: DNA
<213> ORGANISM: Artificial Sequence
<220> FEATURE:
<223> OTHER INFORMATION: Description of Artificial Sequence: Solid Phase
    Synthesis of Nucleic Acid Probes Complementary to
    VRE genes vanA, vanB, vanB2, vanC1, vanC2, vanC3,
    vanD, or variants thereof

<400> SEQUENCE: 7
gaggaacgaa atcgggtgca                                          20

<210> SEQ ID NO: 8
<211> LENGTH: 20
<212> TYPE: DNA
<213> ORGANISM: Artificial Sequence
<220> FEATURE:
<223> OTHER INFORMATION: Description of Artificial Sequence: Solid Phase
    Synthesis of Nucleic Acid Probes Complementary to
    VRE genes vanA, vanB, vanB2, vanC1, vanC2, vanC3,
    vanD, or variants thereof

<400> SEQUENCE: 8
tgcacccgat ttcgttcctc                                          20

<210> SEQ ID NO: 9
<211> LENGTH: 27
<212> TYPE: DNA
<213> ORGANISM: Artificial Sequence
<220> FEATURE:
<223> OTHER INFORMATION: Description of Artificial Sequence: Solid Phase
    Synthesis of Nucleic Acid Probes Complementary to
    VRE genes vanA, vanB, vanB2, vanC1, vanC2, vanC3,
    vanD, or variants thereof

<400> SEQUENCE: 9
gccgacagtc tccccgccat actctcc                                  27

<210> SEQ ID NO: 10
<211> LENGTH: 27
<212> TYPE: DNA
<213> ORGANISM: Artificial Sequence
<220> FEATURE:
<223> OTHER INFORMATION: Description of Artificial Sequence: Solid Phase
    Synthesis of Nucleic Acid Probes Complementary to
    VRE genes vanA, vanB, vanB2, vanC1, vanC2, vanC3,
    vanD, or variants thereof

<400> SEQUENCE: 10
ggagagtatg cgggagac tgtcggc                                    27

<210> SEQ ID NO: 11
<211> LENGTH: 25
<212> TYPE: DNA

```
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 11
ttaataaccc aaaaggcggg agtag                                          25

<210> SEQ ID NO: 12
<211> LENGTH: 25
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 12
taataaccca aaaggcggga gtagc                                          25

<210> SEQ ID NO: 13
<211> LENGTH: 21
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 13
cgagccggaa aaaggctctg a                                              21

<210> SEQ ID NO: 14
<211> LENGTH: 17
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 14
ccggaaaaag gctctga                                                   17

<210> SEQ ID NO: 15
<211> LENGTH: 21
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 15
cgagccggaa aaaggctcag a                                              21

<210> SEQ ID NO: 16
<211> LENGTH: 17
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
```

VRE genes vanA, vanB, vanB2, vanC1, vanC2, vanC3,
          vanD, or variants thereof
<220> FEATURE:
<223> OTHER INFORMATION: Where N at position 15 is an abasic nucleotide,
      a universal nucleotide or a mixture of natural
      nucleotides

<400> SEQUENCE: 16
ccggaaaaag gctcnga                                                   17

<210> SEQ ID NO: 17
<211> LENGTH: 24
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 2 and 5 are an abasic
      nucleotide, a universal nucleotide, or mixture of
      natural nucleotides

<400> SEQUENCE: 17
cncanccgac ctcacagccc gaaa                                           24

<210> SEQ ID NO: 18
<211> LENGTH: 24
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 2 and 5 are an abasic
      nucleotide

<400> SEQUENCE: 18
cncanccgac ctcacagccc gaaa                                           24

<210> SEQ ID NO: 19
<211> LENGTH: 22
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 3 is an abasic nucleotide

<400> SEQUENCE: 19
canccgacct cacagcccga aa                                             22

<210> SEQ ID NO: 20
<211> LENGTH: 22
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<221> NAME/KEY: modified_base
<222> LOCATION: (3)
<223> OTHER INFORMATION: i

<400> SEQUENCE: 20
canccgacct cacagcccga aa                                        22

<210> SEQ ID NO: 21
<211> LENGTH: 23
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 21
acagccgacc tcacagcccg aaa                                       23

<210> SEQ ID NO: 22
<211> LENGTH: 21
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 2 is an abasic residue

<400> SEQUENCE: 22
anccgacctc acagcccgaa a                                         21

<210> SEQ ID NO: 23
<211> LENGTH: 20
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 1 is an abasic residue

<400> SEQUENCE: 23
nccgacctca cagcccgaaa                                           20

<210> SEQ ID NO: 24
<211> LENGTH: 19
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 24
ccgacctcac agcccgaaa                                            19

<210> SEQ ID NO: 25
<211> LENGTH: 22
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 25
cavccgacct cacagcccga aa                                              22

<210> SEQ ID NO: 26
<211> LENGTH: 20
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 26
vccgacctca cagcccgaaa                                                 20

<210> SEQ ID NO: 27
<211> LENGTH: 22
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 3 is 5-nitrindol

<400> SEQUENCE: 27
canccgacct cacagcccga aa                                              22

<210> SEQ ID NO: 28
<211> LENGTH: 20
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof
<220> FEATURE:
<223> OTHER INFORMATION: Where N at position 1 is 5-nitrindol

<400> SEQUENCE: 28
nccgacctca cagcccgaaa                                                 20

<210> SEQ ID NO: 29
<211> LENGTH: 22
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 29
caaccgacct cacagcccga aa                                              22

<210> SEQ ID NO: 30
<211> LENGTH: 22
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 30
cagccgacct cacagcccga aa                    22

<210> SEQ ID NO: 31
<211> LENGTH: 21
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 31
agccgacctc acagcccgaa a                     21

<210> SEQ ID NO: 32
<211> LENGTH: 20
<212> TYPE: DNA
<213> ORGANISM: Artificial Sequence
<220> FEATURE:
<223> OTHER INFORMATION: Description of Artificial Sequence: Solid Phase
      Synthesis of Nucleic Acid Probes Complementary to
      VRE genes vanA, vanB, vanB2, vanC1, vanC2, vanC3,
      vanD, or variants thereof

<400> SEQUENCE: 32
gccgacctca cagcccgaaa                       20

COMPOSITIONS AND METHODS FOR DETECTING VANCOMYCIN RESISTANT ENTEROCOCCI BY CYCLING PROBE REACTIONS

This application claims the benefit of the following provisional applications: Ser. No. 60/051,699, filed Jul. 3, 1997, Ser. No. 60/086,022, filed May 18, 1998, and Ser. No. 60/090,275, filed Jun. 22, 1998, each of which is incorporated herein by reference.

TECHNICAL FIELD

The present invention relates generally to probe sequences and methods for detecting target nucleic acid molecules, and more specifically, to probes for detecting antibiotic vancomycin resistant enterococci ("VRE") and methods thereof.

BACKGROUND OF THE INVENTION

Vancomycin resistant enterococci (VRE) represents a serious problem for healthcare worldwide. For example, the Center for Disease Control (CDC) has released data for antibiotic resistance associated with hospital-caused infections from January 1989 to March 1993, showing a 20-fold increase in the percentage of enterococci that were resistant to the antibiotic vancomycin (MMMWR 42:597–599, 1993) during this period. Both vanA and vanB genes of enterococci have been found to be associated with the increased resistance.

Transfer of the vanA and vanB antibiotic resistance genes to non-enterococcal species is also a growing concern. The vanA gene has been found in Corynebacterium, Arcanobacterium and Lactococcus species (Power et al. *J. Antimicrobiol. Chemother.* 36:595–606, 1995). Recently, Poyart et al. (*Antimicrobiol. Agents Chemotherap.* 41:24–29, 1997), reported an occurrence of a Streptococcus bovis clinical isolate with a VanB resistance phenotype. The gene was shown to be highly homologous to the prototype vanB gene from Enterococcus.

Increased use of antibiotics has resulted in the emergence of vancomycin-resistant microorganisms such as Enterococcus spp. and Staphylococcus spp. (Dutka-Malen et al., *Antimicrobiol. Agents Chemother.* 34:1875–1879, 1990). Vancomycin-resistant *S. aureus* (VISA) is certain to emerge in hospitals with high rates of methicillin resistant *Staphylococcus aureus* (MRSA) and the use of vancomycin (Edmond et al., *Ann. Intern. Med.* 124:329–334, 1996). Recently, VISA isolates have been reported in Latin America (Navarro Marin, *International Journal of Antimicrobial Agents* 7:293–294, 1996).

Briefly, there are four phenotypes of enterococci that can be separated based on expression of constitutive and inducible resistance of the glycopeptides, vancomycin and teicoplanin (Leclercq and Courvalin, *Clin. Infec. Dis.* 24:545–556, 1997). Inducible resistance to high levels of vancomycin (MIC≧64 mg/l) and teicoplanin (MIC≧16 mg/l) is characteristic of the VanA phenotype. This type of resistance is plasmid mediated. The vanA gene has recently been found on mobile elements that can direct their own transfer from the chromosome of one Enterococcus strain to another. The VanB phenotype is described as inducible resistant to vancomycin with MIC of 4 mg/l to ≧1,000 mg/l but displaying susceptibility to teicoplanin. The vanB gene is transferable by conjugation in certain strains. The genes in the VanC phenotype produce constitutive resistance and occur in *E. gallinarum* and *E. casseliflavis* and *E. flavenscens* (Leclercq and Courvalin Supra; Navarro & Courvalin, *Antimirobiol. Agents Chemother.* 38:1788–1793, 1994). Recently, VanD phenotype has been reported and is characterized by moderate levels of vancomycin resistance and low level resistance to teicoplanin (cited in Leclercq and Courvalin Supra).

The majority of conventional methods for detection of glycopeptide resistant enterococci have drawbacks related to time, lack of specificity and sensitivity of detection. For example, detection of the glycopeptide resistant enterococci can be carried out by conventional susceptibility testing (broth and agar methods), but these techniques are slow, and automated detection is not recommended due to poor performance (Aarestrup et al., *Antimicrob. Agents Chemother.* 40:1938–1940, 1996). Although the above methods can be used to detect VRE, there is an urgent need for a rapid, user friendly and reliable method for detecting the vanA gene and vanB genes from VRE, both in the hospital and community settings. The present invention provides probes and methods for detecting the vanA and vanB genes rapidly. Further, the present invention provides other related advantages.

SUMMARY OF THE INVENTION

Briefly stated, the present invention provides compositions and methods for detecting vanA and vanB genes from enterococci.

Within one aspect of the present invention, methods are provided for determining the presence of vancomycin antibiotic resistant gene(s) of enterococci in a biological sample, comprising the steps of (a) treating cells contained within the biological sample to expose single stranded-target nucleic acid molecules; (b) reacting said target single-stranded cellular nucleic acids with one or more scissile-link containing nucleic acid probe(s) which are complementary to one or more portion(s) of the antibiotic vancomycin resistant gene, and with an enzyme molecule, under conditions, which allow the target and probe to hybridize to each other and form one or more double-stranded, target-probe complex(es), said enzyme molecule being capable of cleaving said scissile link of said target-probe complex(es) such that one or more fragments of the nucleic acid probe is released from said complex(es); and (c) determining whether cleaved portions of the nucleic acid probe are produced, and thereby detecting the presence of a vancomycin antibiotic resistant gene. Within various embodiments, determination of whether cleaved probe is produced can be accomplished by directly detecting cleaved portions of the nucleic acid probe, and/or detecting a decrease in the amount of uncleaved probe.

Within various embodiments, the scissile-link containing nucleic acid probe is complementary to a vancomycin resistant gene selected from the group consisting of vanA, vanB, vanB2, vanC1, vanC2, vanC3, vanD, or variants thereof. Within further embodiments, more than one probe may be utilized in order to multiplex, or detect more than one gene per reaction. Representative examples of suitable probes include: TTAATAACCC aaaaGGCGGG AGTAGCT (SEQ ID NO:1); TACATTCTTA CaaaaAATGC GGGCATC (SEQ ID NO:3); GAGGAACgaa aTCGGGTGCA (SEQ ID NO:7); and GCCGACAGTC TccccGCCA TACTCTCC (SEQ ID NO:9).

Within further embodiments, a single probe may be utilized in order to detect multiple genes (e.g., any one of the vanA, van B or vanB2) per reaction. Representative examples of suitable probes include $CN^1CAN^2CCG$ ACCT-CacagC CCGAAA (SEQ ID NO:17) and modifications thereof, wherein $N_1$ and $N_2$ can be a combination of bases typical of vanA, vanB and vanB2, abasic sites or universal bases.

Within other related aspects of the present invention, probes for detecting the presence of a vancomycin antibiotic resistant gene in a biological sample are provided, wherein said probe comprises at least a portion of a sequence which specifically recognizes a vancomycin resistant gene (e.g., Sequence ID Nos.1, 3, 9 or 17). Also provided are kits which comprise such probes, along with an enzyme (e.g., RNase H) which cleaves scissile links.

Also provided by the present invention are kits for detecting the presence of a vancomycin-resistant gene in a biological sample, comprising (a) one or more scissile-link containing nucleic acid probes which bind to a vancomycin-resistant gene, and (b) an enzyme capable of cleaving the scissile link when the probe is bound to the target. Within a further embodiment, the gene is selected from group consisting of vanA, vanB, vanB2, vanC1, vanC2, vanC3, vanD, and variants thereof. Within a related embodiment, more than one vancomycin antibiotic resistant gene is detected simultaneously. With further embodiments, the enzyme is RNase H.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

DETAILED DESCRIPTION OF THE INVENTION

DEFINITIONS

Figure 1:
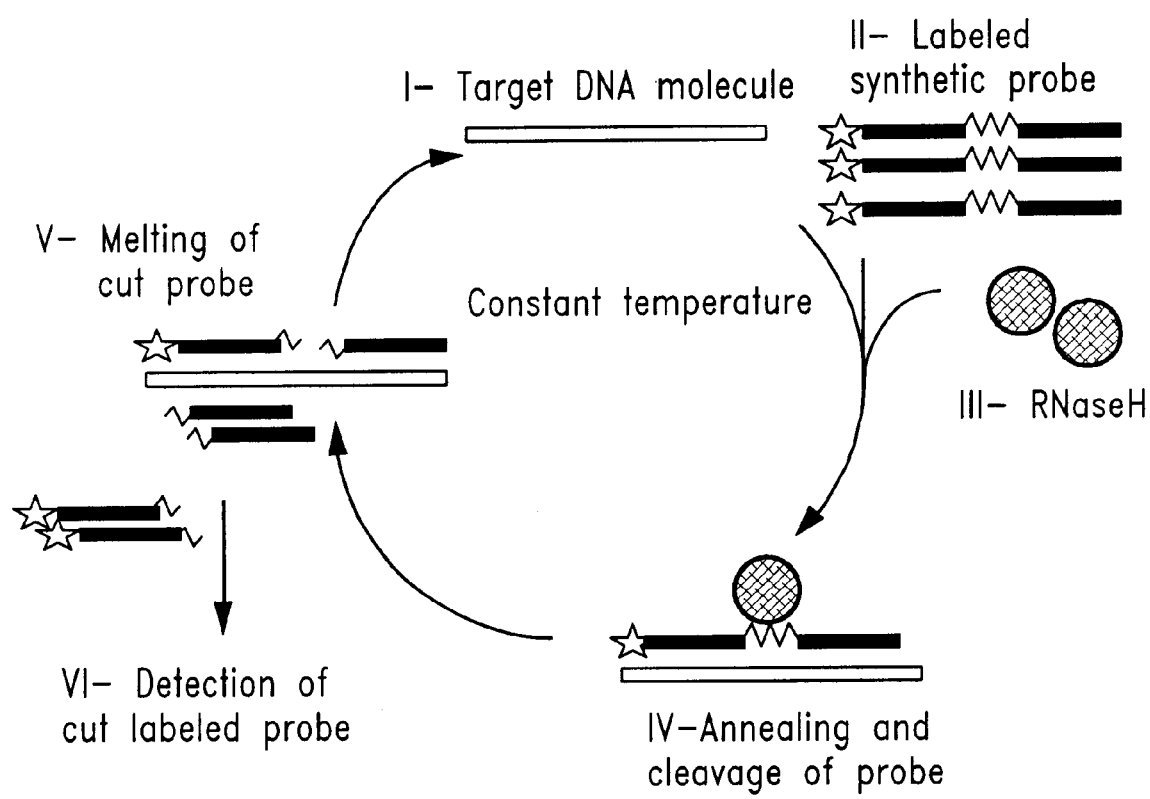
FIG. 1 is a schematic illustration of one representative embodiment of a cycling probe reaction.

"Nucleic acid molecule" refers to a polymeric nucleotide or polynucleotide, which can have a natural or synthetic origin. Representative examples of nucleic acid molecules include DNA (ds- or ss-DNA), RNA, DNA-RNA hybrids, or nucleic acid molecules which are composed of or contain a nucleic acid analogue (e.g., α-enantiomeric forms of naturally-occurring nucleotides). Furthermore, nucleotides may be modified in their sugar moieties, or in the pyrimidine or purine base moieties. Examples of modification to sugar moities include modification or replacement of, for example, one or more hydroxyl groups with another group. Modifications to base moieties include alkyl or acylated pyrimidines and purines. In addition, nucleic acid monomers can be linked by phosphodiester bonds, or analogs of such linkages (e.g., phosphorothioate, phosphorodithioate, phosphoramidite, and the like.

"Isolated nucleic acid molecule" refers to a nucleic acid molecule that is not integrated into the genomic DNA of an organism. Isolated nucleic acid molecules include, for example, probes and other synthetically or recombinantly generated nucleic acid molecules.

"Scissile linkage" refers to a nucleic acid molecule which is capable of being cleaved or disrupted without cleaving or disrupting any nucleic acid sequence of the molecule itself or of the target nucleic acid sequence. Scissile linkages include any connecting chemical structure which joins two nucleic acid sequences and which is capable of being selectively cleaved without cleavage of the nucleic acid sequences to which it is joined. The scissile linkage may be a single bond or a multiple unit sequence. An example of such a chemical structure is an RNA sequence. Other chemical structures suitable as a scissile linkage are a DNA sequence, an amino acid sequence, an abasic nucleotide sequence or an abasic nucleotide, or any carbohydrate polymer, i.e., cellulose or starch. When the scissile linkage is a nucleic acid sequence, it differs from the nucleic acid sequences of $NA_1$ and $NA_2$ (described below).

"Probe Containing a Scissile Linkage" refers to a synthetic nucleic acid molecule which is constructed in view of a known sequence to be complementary or substantially complementary to a target nucleic molecule. Within certain embodiments, the probe comprises the structure $[NA_1—S—NA_2]_n$ wherein $NA_1$ and $NA_2$ are different, non-complementary nucleic acid molecules and S is a scissile linkage, and n is an integer from 1 to 10.

"Ribonuclease H" ("RNase H") refers to an enzyme capable of specifically cleaving the RNA strand in RNA:DNA hybrid duplex (see generally Crouch & Dirksen in Nucleases, Linn & Roberts (Eds.), pp. 211–241, Cold Spring Harbour Laboratory Press, Plainview, N.Y., 1982).

"Universal base" refers to a base capable of pairing with each of the natural bases, adenine, guanine, cytosine and thymine in a duplex or alternatively it is not capable of pairing but does not destablize the opposite base in a duplex. Some examples of universal bases are inosine, indole, 5-nitroindole, 3-nitropyrrole and 5-nitropyrrole. A chimeric oligonucleotide probe can be synthesized to contain one or more universal base(s) at the appropriate position(s) matching mismatch(es) of one or more target sequences.

"Abasic nucleotide" or "Abasic site" refers to deoxyribonucleotide or ribonucleotide without the base portion. A chimeric oligonucleotide probe can be synthesized to contain abasic site at the appropriate position(s) matching mismatch(es) of one or more target sequences.

As noted above, the present invention provides methods for determining the presence of vancomycin resistant gene(s) of enterococci in a biological sample, comprising the steps of (a) treating cells contained within the biological sample to expose single stranded-target nucleic acid molecules; (b) reacting said target single-stranded cellular nucleic acids with a scissile-link containing nucleic acid probe which is complementary to a portion of the antibiotic vancomycin resistant gene, and with an enzyme molecule, under conditions, which allow the target and probe to hybridize to each other and form a double-stranded, target-probe complex, said enzyme molecule being capable of cleaving said scissile link of said target-probe complex such that one or more fragments of the nucleic acid probe is released from said complex; and (c) determining whether cleaved portions of the nucleic acid probe are produced, and thereby detecting the presence of a vancomycin antibiotic resistant gene.

Such methods may be utilized to detect the presence of a desired target nucleic acid molecule within a wide variety of biological samples. Representative examples of biological samples include clinical samples (e.g., blood, urine, stool, or abscess) and clinical samples grown and/or isolated on a bacteriological growth medium. Methods for generating target nucleic acid molecules may be readily accomplished by one of ordinary skill in the art given the disclosure provided herein (see generally, Sambrook et al., *Molecular Cloning: A Laboratory Manual* (2d ed.), Cold Spring Harbor Laboratory Press, 1989).

As noted above, within one aspect of the present invention the target nucleic acid molecule is reacted with a complementary single-stranded nucleic acid probe having a scissile linkage. Briefly, a wide variety of nucleic acid probes having scissile linkages may be utilized within the context of the present invention. Preferably, the probe is designed such that, upon cleavage by an enzyme which is capable of specifically cleaving the probe-target complex at the scissile link, probe portions are released which are detectable (see U.S. Pat. Nos. 4,876,187, 5,011,769 and 5,403,711). Preferred probe molecules of the present invention generally have the structure $[(NA_1)_x (—S—)_z (—NA_2)_y]_n$ wherein $NA_1$ and $NA_2$ are molecules composed of nucleic acids or nucleic acid analogues, —S— is a scissile linkage and x, y, and z are integers from 1–100 and n is an integer from 1–10. Within certain particularly preferred embodiments of the invention, $NA_1$ and $NA_2$ may range from 3 to 40 nucleotides, and when S is composed of nucleic acids, may range in size from 2 to 20 nucleotides. In addition, it should be understood that as utilized within the context of the present invention, each of x, y and z can vary with each iteration of n. Although within various embodiments of the invention a single-stranded probe is utilized to react or hybridize to a single-stranded target sequence, the above-described methods should not be limited to only situations wherein complementary probe and target sequences pair to form a duplex.

Within one embodiment, $NA_1$ and $NA_2$ as described above are DNA molecules which may or may not have the same sequence. Alternatively, $NA_1$ and $NA_2$ may be constructed of RNA molecules, which may or may not have the same sequence, or a combination of RNA and DNA molecules. The DNA or RNA molecules utilized may be derived from naturally occurring sources, or they may be synthetically formed. Each of $NA_1$ and $NA_2$ may be from about 5 bases to 10,000 bases in length.

Within other embodiments, $NA_1$ or $NA_2$ may be composed of nucleic acid analogues such as methyl phosphonates, carbamates, amidates, triesters, or "Peptide Nucleic Acids" ("PNA"). For example, PNA oligomers can hybridize to complementary target oligonucleotides (DNA or RNA) sequences with very high specificity. Such duplexes are more stable than the corresponding DNA-DNA or DNA-RNA duplexes (Egholm et al., *Nature* 365:556–568, 1993). Furthermore, PNA can bind to double stranded (ds) DNA by strand displacement (Nielsen et al., *Science* 254:1497–1500, 1991) and hence may obviate the traditional double strand denaturation requirement in sample preparation. Low concentration salt is generally preferred for binding of PNA to dsDNA ($\leq 50$ mM/L of $Na^+$). Moderate concentration of salt can inhibit binding through double strand displacement of PNA to dsDNA. However, once bound the PNA/DNA duplexes are stable to high concentration of salt. Further, these duplexes are also thermally stable compared to oligonucleotide/oligonucleotide duplexes (duplexes of PNA/DNA are more stable by approximately 1° C. per base pair compared to corresponding DNA/DNA). Based on the requirement of high sequence specificity to the target oligonucleotide, greater thermal stability and resistance to high salt concentration of the duplex once formed, PNAs are often ideal molecules for use in the methods described herein. Within certain embodiments, two short PNAs may be linked with scissile linkage and used as a highly sequence specific probe.

Single stranded nucleic acid molecules may be obtained and/or prepared directly from a target cell or organism utilizing standard techniques (see, e.g., Sambrook et al., "Molecular Cloning: A Laboratory Manual", Cold Spring Harbor, 1989), or prepared utilizing any of a wide variety of a techniques, including for example, PCR, NASBA, reverse transcription of RNA, SDA, branched-chain DNA and the like.

Probes of the present invention may also have one or more detectable markers attached to one or both ends (e.g., $NA_1$ or $NA_2$). The marker may be virtually any molecule or reagent which is capable of being detected, representative examples of which include radioisotopes or radiolabeled molecules, fluorescent molecules, fluorescent antibodies, enzymes, or chemiluminescent catalysts. Within certain embodiments of the invention, the probe may contain one or more labels such as a fluorescent or enzymatic label (e.g., quenched fluorescent pairs, or, a fluorescent label and an enzyme label), or a label and a binding molecule such as biotin (e.g., the probe, either in its cleaved or uncleaved state, may be covalently or non-covalently bound to both a label and a binding molecule (see also, e.g., U.S. Pat. No. 5,731,146).

Within certain variants, the probe and target nucleic acid molecule need not be perfectly complementary, and indeed, may be purposely different by one, two, three or more nucleic acids (see, e.g., PCT Publication WO 95/14106 and U.S. Pat. No. 5,660,988). Within further variants, the target nucleic acid molecule is present in a heterogeneous population of genomic nucleic acids.

As noted above, the nucleic acid probe has a scissile linkage which is capable of being cleaved or disrupted without cleaving or disrupting any nucleic acid sequence of the molecule itself, or of the target nucleic acid sequence. As used within the context of the present invention, a scissile linkage is any connecting chemical structure which joins two nucleic acid sequences, and which is capable of being selectively cleaved without cleavage of the nucleic acid sequences to which it is joined. The scissile linkage may be a single bond or a multiple unit sequence. An example of such a chemical structure is an RNA molecule. Other chemical structures which may be suitable as a scissile linkage are DNA molecules, an amino acid sequence, an abasic nucleotide molecule or any carbohydrate polymer (e.g., cellulose or starch). When the scissile linkage is a nucleic acid molecule, it should differ from the nucleic acid sequence of $NA_1$ and $NA_2$.

In the nucleic acid probes described above, when n is greater than one, the unit $NA_1$—S—$NA_2$ repeats. As should be readily understood by one of ordinary skill in the art given the disclosure provided herein, the unit may be the same within each repeat, or may vary randomly in a defined pattern. In addition, the scissile linkage may also vary from unit to unit. For example, one scissile linkage may be an amino acid sequence, and another an RNA molecule.

As noted above, the probes of the present invention may also be linked to a solid support either directly, or through a chemical linker. Representative examples of solid supports include silicaceous, cellulosic, polymer-based, or plastic materials.

Within a particularly preferred embodiment of the invention, nucleic acid probes have the structure: $[NA_1$—S—$NA_2]_n$ wherein $NA_1$ and $NA_2$ are nucleic acid sequences, S is a scissile nucleic acid linkage, and n is an integer from 1 to 10. Within this embodiment, $NA_1$ and $NA_2$ are different nucleic acid sequences which are noncomplementary to each other, and —S— is a scissile linkage which is capable of being cleaved or disrupted without cleaving or disrupting $NA_1$ or $NA_2$, or a target nucleic acid sequence capable of hybridizing to the $NA_1$ or $NA_2$ sequences, wherein if the scissile linkage is a nucleic acid sequence it is RNA when both $NA_1$ and $NA_2$ are DNA sequences, or the scissile linkage is DNA when both $NA_1$ and $NA_2$ are RNA sequences.

Methods for constructing such nucleic acid probes may be readily accomplished by one of ordinary skill in the art, given the disclosure provided herein.

Nucleic acid molecules useful in the methods of the present invention can be constructed on a solid support medium (such as silica gel or controlled pore glass) using either a hydrolysable linkage or a permanent (non-hydrolysable) linkage. Published chemical methods were used for this synthesis. Oligonucleotide molecules are constructed as generally described by Matteucci and Caruthers, *J. Am. Chem. Soc.* 103:3185, 1981; Beaucage and Caruthers, *Tetrahedron Lett.* 22:1859, 1981; Alvarado-Urbina et al., "Automated Synthesis of Gene Fragments," *Science* 214:270–274, 1981; see also U.S. Pat. Nos. 4,876,187, 5,011,769 and 5,403,711. For oligonucleotide analogs and conjugates synthesis see generally Agrawal (ed.) *Protocols For Oligonucleotides And Analogs, Synthesis; Synthesis and Properties,* Methods in Molecular Biology Volume 20, Humana Press Inc., 1993; Egholm et al., *Nature* 365:566–568, 1993; Dueholm et al., *J. Org. Chem.* 59:5767–5773, 1994; Agrawal (ed.) *Protocols For Oligonucleotide Conjugate, Synthesis And Analytical Techniques,* Methods in Molecular Biology Volume 26, Humana Press Inc., 1994. For non-isotopic probes see generally Kriscka, *Non-Isotopic DNA Probe Techniques,* Academic Press Inc., New York, 1992.

Particularly preferred probes (and synthetic targets) are based on the vanA, vanB, vanB2 genes published by Dutka-Malen et al., *Mol. Gen. Genet.* 224:364–372, 1990 (GenBank accession No. X56895), Evers et al., *Gene* 140:97–102, 1994 (GenBank Accession No. U00456) and GenBank Accession No. Z83305 Gold et al. (*Antimicrobiol. Agents Chemother.* 37:1604–1609, 1993) has also published vanB2 sequence (GenBank Accession No. L15304). More preferred probes are single probes that are capable of detecting any one of vanA, vanB or vanB2 genes, based on common sequences or modification such as use of abasic or universal nucleotides at mismatch positions in the sequences thereby allowing for the detection of these genes.

Briefly, oligonucleotide synthesis is accomplished in cycles wherein each cycle extends the oligonucleotide by one nucleotide. Each cycle consists of four steps: (1) deprotecting the 5'-terminus of the nucleotide or oligonucleotide on the solid support; (2) coupling the next nucleoside phosphoroamidite to the solid phase immobilized nucleotide; (3) capping the small percentage of the 5'-OH groups of the immobilized nucleotides which did not couple to the added phosphoramidite; and (4) oxidizing the oligonucleotide linkage to a phosphotriester linkage.

Representative methods for synthesizing oligonucleotides and biotinylation and fluoresceination of the oligonucleotides are shown in Example 1.

Design And Synthesis Of A Single Chimeric Probe
For Simultaneous Detection Of Any Of The
Enterococcal vanA Or vanB or vanB2 Genes Two regions of vanA and vanB genes were considered for the design and synthesis of probes. Region #1 resulted in design and synthesis of vanABmod2-24 probe (SEQ ID NO:18; IDB Seq. No. 450, see below) and other probes based on subsequence and/or modifications as described below. Region #2 resulted in design and synthesis of four probes, vanA111-17 (SEQ ID NO:13; IDB Seq. No. 434), vanA1121-17 (SEQ ID NO:14; IDB Seq. No. 442), vanB799-21 (SEQ ID NO:15; IDB Seq. No.435), and vanABmod1-17 (SEQ ID NO:16; IDB Seq. No.443).

For Region #1, with the exceptions of two nucleotides labeled as $N^1$ and $N^2$ (mismatches) the following oligonucleotide sequence overlaps with the genes of vanA, vanB and vanB2:

5'-CN$^1$CAN$^2$CCGACCTCacagCCCGAAA-3' (SEQ ID NO:17)

The differences in the sequences for the vanA, vanB and vanB2 genes and the complementary probes are detailed as follows:

for vana gene $N^1=T, N^2=T$, then probe would be for $N^1=A$, $N^2=A$;

for vanB gene $N^1=C, N^2=C$, then probe would be $N^1=G$, $N^2=G$; and for vanB2 gene $N^1=T, N^2=G$, then probe would be $N^1=A$, $N^2=C$.

The above basic probe sequence (SEQ ID NO:17) can be modified in a number of ways in order to design a single probe that can simultaneously detect all of the above genes and the following are some representative examples of the modifications:

A) Combination of bases typical of either vanA, vanB or vanB2 genes

Where in SEQ ID NO:17 $N^1=A$ (i.e., typical of vanA and vanB2) and $N^2=G$ (i.e., typical of vanB) resultant probe: vanABmod5-23 probe (SEQ ID NO:21; IDB Seq. No. 476).

B) Shorter length probes

The following are examples of shorter length probes: vanABmod3-22 (SEQ ID NO:19; IDB Seq. No. 477), vanB687-22 (SEQ ID NO:30; IDB Seq. No. 534), vanABmod6-21 (SEQ ID NO:22; IDB Seq. No. 494), vanB687-21 (SEQ ID NO: 31; IDB Seq. No. 535), vanABmod7-20 (SEQ ID NO:23; IDB Seq. No. 493), vanB687-20 (SEQ ID NO:32; IDB Seq. No. 536), and vanABmod8-19 (SEQ ID NO: 24; IDB Seq. No. 492).

C) Chemically modified bases in the position of mismatch

The following probes have been modified at $N^1$ and $N^2$ positions: vanABmod2-24 (SEQ ID NO:18; IDB Seq. No. 450) has $N^1$ and $N^2$ as abasic sites; vanABmod3-22 (SEQ ID NO:19; IDB Seq. No. 477), vanABmod6-21 (SEQ ID NO: 22; IDB Seq. No. 494), and vanABmod7-20 (SEQ ID NO:23; IDB Seq. No. 493) has $N^2$ as abasic site; vanABmod4-22 (SEQ ID NO:20; IDB Seq. No. 478) has $N^2$ as a universal base, inosine; vanABmod9-22 (SEQ ID NO:25) and vanABmod9-20 (SEQ ID NO:26) has $N^2$ as mixture of three bases (i.e., 33% of each of A, G, C); and vanABmod10-22 (SEQ ID NO:27) and vanABmod10-20 (SEQ ID NO:28) has $N^2$ as a universal base, 5-Nitroindole.

For sequences based on Region #2, the following two probes were synthesized for single probe VRE assay. These probes have the same sequences except for one base which is indicated by underline:

vanA1117-21 (SEQ ID NO:13; IDB Seq. No. 434)
CGAGCCGGaaaaAGGCTC<u>T</u>GA
vanB799-21 (SEQ ID NO:15; IDB Seq. No. 435)
CGAGCCGGaaaaAGGCTC<u>A</u>GA The above probes were further modified as follows:
1) the length of probe was shortened and represented by vanA1121-17 (SEQ ID NO:14; IDB Seq. No. 442)
2) chemically modified base as an abasic site in the position of mismatch and represented by vanABmod1-17 (SEQ ID NO:16; IDB Seq. No. 443).

Detection Reactions

As noted above, cycling reactions for the detection of a desired target nucleic acid molecule may be readily performed according to the general steps set forth above (see also, U.S. Pat. Nos. 5,011,769 and 5,403,711).

Other cycling reactions which may be performed include reacting a target nucleic acid molecule, a complementary single-stranded nucleic acid probe having a scissile linkage, under conditions which allow the probe to hybridize to the target nucleic acid and form a double-stranded, target-probe complex.

The compositions and methods provided herein may be utilized in a wide variety of other/related methods (e.g., U.S. Pat. Nos. 5,210,015; 5,487,972; 5,422,253; 5,691,142; 5,719,028; 5,130,238; 5,409,818; 5,554,517; 5,589,332, 5,399,491; 5,480,784; 5,215,899; 5,169,766; 5,194,370; 5,474,916; 5,698,400; 5,656,430; and PCT publication nos. WO 88/10215; WO 92/08800; WO 96/02668; WO 97/19193; WO 97/09444; WO 96/21144; WO 92/22671). Other variations of this assay include 'exponential' cycling reactions such as described in U.S. Pat. No. 5,403,711 (see also U.S. Pat. No. 5,747,255).

Representative examples of further suitable assay formats including any of the above assays which are carried out on solid supports such as dipsticks, magnetic beads, and the like (see generally U.S. Pat. Nos. 5,639,428; 5,635,362; 5,578, 270; 5,547,861; 5,514,785; 5,457,027; 5,399,500; 5,369, 036; 5,260,025; 5,208,143; 5,204,061; 5,188,937; 5,166, 054; 5,139,934; 5,135,847; 5,093,231; 5,073,340; 4,962, 024; 4,920,046; 4,904,583; 4,874,710; 4,865,997; 4,861, 728; 4,855,240; and 4,847,194).

Within certain embodiments of the invention, cycling probe reactions may be performed utilizing additives such as polyamines (e.g., spermine) or ribosomal proteins which increase sensitivity, specificity, and/or rate of reaction. These, as well as other related aspects are described in U.S. Provisional applications entitled "ADDITIVES FOR USE IN CYCLING PROBE REACTIONS," filed May 18, 1998 (Attorney's Docket Nos. 480094.419P2); and "METHODS FOR accelerating HYBRIDIZATION OF NUCLEIC ACID MOLECULES," filed May 18, 1992 (Attorney's Docket No. 480094.422P2).

The following examples are offered by way of illustration, and not by way of limitation.

EXAMPLES

Example 1

Construction of Nucleic Acid Probes

Nucleic acid molecules can be synthesized utilizing standard chemistries on automated, solid-phase synthesizers such as PerSeptive Biosystems Expedite DNA synthesizer (Boston, Mass.), PE Applied Biosystems, Inc.'s Model 391 DNA Synthesizer (PCR-MATE EP) or PE Applied Biosystems, Inc.'s Model 394 DNA/RNA Synthesizer (Foster City, Calif.). Preferably, PerSeptive Biosystems Expedite DNA synthesizer is used and the manufacturer's modified protocol for making oligonucleotides is carried out.

Reagents for synthesis of oligonucleotides are commercially available from a variety of sources including synthesizer manufacturers such as PerSeptive Biosystems, PE Applied Biosystems Inc., Glen Research (Sterling, Va.) and Biogenex. For DNA and RNA synthesis, the preferred fluorescein amidite, phosphoramidites of deoxy-and ribonucleosides, 2'-O-methyl and reagents, such as activator, Cap A, Cap B. oxidizer, and trityl deblocking reagent are available from PerSeptive Biosystems. Biotin-TEG-phosphoroamidite and Biotin-TEG-CPG are available from Glen Research. Ammonium hydroxide (28%) used for the deprotection of oligonucleotides is purchased from Aldrich. 1 M Tetrabutylammonium fluoride (TBAF) used for removing the 2'-O-tert-butyldimethylsilyl group is purchased from Aldrich and used after drying over molecular sieves for 24 hours. All buffers are prepared from autoclaved water and filtered through 0.2 $\mu$m filter.

The following procedure is used for preparing biotinylated and/or fluoresceinated oligonucleotides. Biotin-TEG- CPG (1 μmol) is packed into a synthesis column. Nucleoside phosphoramidites are then linked to make the defined nucleic acid sequence using PerSeptive Biosystem's modified protocol for making oligonucleotides. Fluorescein-amidite is dissolved in acetonitrile to a final concentration of 0.1 M. The fluorescein amidite is loaded on the synthesizer and added to the 5'- end of the oligonucleotide. Alternatively, phosphoramidite containing thio-linker is added at the 5'- terminal of the chimeric probe using the modified protocol. After the deprotection step described below, the probe is purified by reverse phase HPLC using Millipore's R-2 resin which retains the trityl containing oligonucleotide. In order to generate free reactive thio-group, the HPLC purified probe is treated with silver nitrate for 90 minutes at room temperature followed by neutralization of silver nitrate with dithiotheritol (DTT). The fluorescein-maleimide is then added to the free thio-group of the probe and then purified either by HPLC or by electrophoresis as described below.

After the synthesis of the oligonucleotide sequence, the resin bound oligonucleotide is treated initially with 25% ethanol-ammonium hydroxide (4 ml) at room temperature for 1 hour and subsequently at 55° C. for 16 hours in a closed tube. The tube is cooled, supernatant removed and concentrated to dryness in order to remove ammonia. The residue is dissolved in 1 ml of water and filtered through a 0.2 μm filter. The $OD_{260}$ is determined and an aliquot of approximately 2 $OD_{260}$ units is injected into the R-2 column of Biocad's HPLC to obtain a base line on the chromatogram for the tert-butyldimethylsilyl groups of the chimeric probe.

The remaining probe solution is lyophilized by centrifugal vacuum evaporator (Labconco) in a 1.5 ml microcentrifuge tube. The resulting oligonucleotide residue is deprotected with 1.0 M TBAF for 24 hours. To determine the extent of desilylation which has taken place, an aliquot of the TBAF reaction mixture is injected into the HPLC (R-2 column) using a linear gradient of 0 to 60% acetonitrile in 50 mM triethylammonium acetate (TEAA), pH 6.5. If only a partial desilylation has occurred, the TBAF reaction mixture is allowed to proceed for an additional 12 to 16 hours for complete removal of the protecting groups. The TBAF reaction mixture is quenched with 100 mM NaOAc, pH 5.5 and evaporated to dryness. The crude oligonucleotide product is desalted on a P-6 column (2 cm×10 cm, Bio-Rad), the fractions are concentrated to approximately 1 ml and the concentration measured at $OD_{260}$.

The crude oligonucleotide is purified by polyacrylamide gel electrophoresis (PAGE) using 20% polyacrylamide-7 M urea. The running gel buffer is 1×TBE (Tris-Borate- ethylenediamine tetraacetic acid (EDTA), pH 8.3) and the electrophoresis is carried out at 50 mA current for 3.5 to 4 hours. The oligonucleotide band is visualized with UV light, excised, placed in a 15 ml plastic conical tube and extracted by crushing and soaking the gel in 5 m of 50 mM NaOAc (pH 5.5) for approximately 12 hours. The tubes are then centrifuged at 3000 RPM and the supernatant carefully removed with a Pasteur pipette. The gel is rinsed with 2 ml of the extraction buffer to remove any residual product. The combined extract is concentrated to a volume of approximately 1 ml and desalted on a P-6 column. The fractions containing the probe are pooled and concentrated to a final volume of approximately 2 ml. The analytical purity of oligonucleotides is checked by labeling the 5'- end of oligonucleotide with [γ$^{32}$P]-ATP and T4-polynucleotide kinase and then running the labeled oligonucleotide on PAGE. $OD_{260}$ is measured using Hewlett Packard's 845X UV spectrophotometer. The oligonucleotide solution is filtered through a 0.2 μm filter and stored at −20° C.

Utilizing the above procedures, the following oligomers were synthesized (upper case letters have been utilized to denote deoxyribonucleotides, and lower case letters have been utilized to denote ribonucleotides):

vanA811L-27 Probe Sequence (SEQ ID NO:1; IDB Seq. No. 143)
    5'-TTAATAACCCaaaaGGCGGGAGTAGCT-3'
vanA811L-27T Target Sequence (SEQ ID NO:2; IDB Seq. No. 144)
    5'-AGCTACTCCCGCCTTTTGGGTTATTAA 3'
van467-27 Probe Sequence (SEQ ID NO:3; IDB Seq. No. 294)
    5'-TACATTCTTACaaaaAATGCGGGCATC-3'
vanB467-27-T Target Sequence (SEQ ED NO:4; IDB Seq. No. 295)
    5'-GATGCCCGCATTTTTTGTAAGAATGTA-3'
vanB242-27 Probe Sequence (SEQ ID NO:5; IDB Seq. No. 133)
    5'-GCCGATAGTCTccccGCCATATTCTCC-3'
vanB242-27T Target Sequence (SEQ ID NO:6; IDB Seq. No. 137)
    5'-GGAGAATATGGCGGGGAGACTATCGGC-3'
vanB857-20 Probe Sequence (SEQ ID NO:7; IDB Seq. No. 292)
    5'-GAGGAACgaaaTCGGGTGCA-3'
vanB857-20T Target Sequence (SEQ ID NO:8; IDB Seq. No. 293)
    5'-TGCACCCGATTTCGTTCCTC-3'
vanB2242-27 Probe Sequence (SEQ ID NO:9; IDB Seq. No. 267)
    5'-GCCGACAGTCTccccGCCATACTCTCC-3'
vanB2242-27T Target Sequence (SEQ ID NO:10; IDB Seq. No.289)
    5'-GGAGAGTATGGCGGGGAGACTGTCGGC-3'
vanA813L-25 Probe Sequence (SEQ ID NO:11; IDB Seq. No. 383)
    5'-TTAATAACCCaaaaGGCGGGAGTAG-3'
vanA812L-25 Probe Sequence (SEQ ID NO:12; IDB Seq. Nos. 359, 394)
    5'-TAATAACCCaaaaGGCGGGAGTAGC-3'
vanA1117-21 (SEQ ID NO:13; IDB Seq. No. 434)
    5'-CGAGCCGGaaaaAGGCTC<u>T</u>GA-3'
vanA1121-17 (SEQ ID NO:14; IDB Seq. No. 442)
    5'-CCGGaaaaAGGCTC<u>T</u>GA-3'
vanB799-21 (SEQ.ID NO:15; IDB Seq. No. 435)
    5'-CGAGCCGGaaaaAGGCTC<u>A</u>GA-3'
vanABmod1-17 (SEQ ID NO:16; IDB Seq. No. 443)
    5'-CCGGaaaaAGGCTCN$^3$GA-3'
    where N$^3$ can be an abasic nucleotide, universal nucleotide, or a mixture of natural nucleotides
SEQ ID NO:17
    5'-CN$^1$CAN$^2$CCGACCTCacagCCCGAAA-3'
    Where N$^1$ and N$^2$ can be an abasic nucleotide, universal nucleotide, or a mixture of natural nucleotides
vanABmod2-24 (SEQ ID NO:18; IDB Seq. No. 450)
    5'-CN$^1$CAN$^2$CCGACCTCacagCCCGAAA-3'
    where N$^1$ and N$^2$ are abasic
vanABmod3-22 (SEQ ID NO:19; IDB Seq. No. 477)
    5'-CAN$^2$CCGACCTCacagCCCGAAA-3'
    where N$^2$ is abasic
vanABmod4-22 (SEQ ID NO:20; IDB Seq. No. 478)
    5 '-CAN$^2$CCGACCTCacagCCCGAAA-3'
    where N$^2$ is inosine vanABmod5-23 (SEQ ID NO:21; IDB Seq. No. 476)
    5'-ACAGCCGACCTCacagCCCGAAA-3'
vanABmod6-21 (SEQ ID NO:22; IDB Seq. No. 494)
    5'-AN²CCGACCTCacagCCCGAAA-3'
    where $N^2$ is abasic
vanABmod7-20 (SEQ ID NO:23; IDB Seq. No. 493)
    5'-N²CCGACCTCacagCCCGAAA-3'
    where $N^2$ is abasic
vanABmod8-19 (SEQ ID NO:24; IDB Seq. No. 492)
    5'-CCGACCTCacagCCCGAAA-3'
vanABmod9-22 (SEQ ID NO:25)
    5'-CAN²CCGACCTCacagCCCGAAA-3'
    where $N^2$ is mixture of A, G and C
vanABmod9-20 (SEQ ID NO:26)
    5'-N²CCGACCTCacagCCCGAAA-3'
    where $N^2$ is mixture of A, G and C
vanABmod10-22 (SEQ ID NO:27)
    5'-CAN²CCGACCTCacagCCCGAAA-3'
    where $N^2$ is 5-nitrindole
vanABmod10-20 (SEQ ID NO:28)
    5'-N²CCGACCTCacagCCCGAAA-3'
    where $N^2$ is 5-nitrindole
vanA1005-22 (SEQ ID NO:29; IDB Seq. No. 533)
    5'-CAACCGACCTCacagCCCGAAA-3'
vanB687L-22 (SEQ ID NO:30; IDB Seq. No. 534)
    5'-CAGCCGACCTCacagCCCGAAA-3'
vanB687L-21 (SEQ ID NO:31; IDB Seq. No. 535)
    5'-AGCCGACCTCacagCCCGAAA-3'
vanB687L-20 (SEQ ID NO:32; IDB Seq. No. 536)
    5'-GCCGACCTCacagCCCGAAA-3'

Example 2

Preparation of Nucleic Acid Target Molecules from Bacterial Source

The following example describes the source of isolates, in house screening for enterococcal phenotypes, purification of genomic DNA from vancomycin resistant and sensitive isolates, and preparation of bacterial lysates.
1. Enterococcal Source Vancomycin resistant and sensitive enterococcal (VRE and VSE) isolates were obtained from the following sites: 66 isolates from Mt. Sinai Hospital (Toronto, ON), 48 isolates from Wishard Memorial Hospital (Indianapolis, Ind.), 121 isolates from Cleveland Clinic Foundation (Cleveland, Ohio), 28 isolates from Vancouver General Hospital (Vancouver, BC), 143 isolates from Graduate Hospital (Philadelphia, Pa.), and 34 isolates from Royal University Hospital (Saskatoon, SK). There were approximately 440 enterococcal isolates available for screenings.

All isolates used in the following examples were tested with National NCCS Standardized antibiotic susceptibility testing with disc diffusion to vancomycin and teicoplanin, MIC to vancomycin and teicoplanin by E Test (AB Biodisc, Solna, Sweden) and assayed by VRE screening agar (PML Microbiological).
2. Purification of Genomic Enterococcal DNA The following description is the procedure for purification of genomic DNA from VRE and VSE as essentially described generally by Marmur, Meth. Enzymol. 100:726–738, 1989). The isolates used for the purification were a vancomycin resistant VanA (IDB No. 339 obtained from Mt. Sinai Hospital), VanB Enterococcus faecalis (ATCC 51299, American Type Culture Collection, Rockville, Md.), and vancomycin sensitive E. faecalis (VSE, ATCC 29212) isolate. Enterococcal isolates for genomic preparation were grown overnight at 37° C. on 5% sheep blood trypticase soy agar (blood TSA) plates. A pre-culture is prepared by inoculating a single colony into 40 ml of Brain Heart Infusion (BHI) broth and grown for 6 to 8 hours at 37° C. This pre-culture is then added to a 1 liter of BHI broth and grown overnight at 37° C. with shaking. The cells are pelleted and washed once with 2% glucose, 1 mM ethylenediamine tetracetic acid (EDTA) and 10 mM Tris, pH 8.1 (TEG) buffer at 6800×g (Sorvall) for 5 minutes at 5° C. to 10° C. Lysis of cells is carried out by addition of 5 mg/ml of lysozyme (Sigma Chemical Company, St. Louis, Mo.) and incubation at 37° C. for 1 hr with shaking. Sodium dodecyl sulfate (SDS, 20%, electrophoretic grade) is added to a final concentration of 0.09%, and the suspension is mixed and incubated in a water bath at 50° C. to 60° C. for 10 minutes and held at room temperature for 1 hour. This is followed by addition of 24 ml of 5 M NaClO$_4$ and 40 ml of 25:24:1 of phenol:chloroform:isoamyl alcohol (v/v, PCIAA), and shaken for 2 hours at room temperature. The emulsion is aliquoted into sterile 30 ml glass tubes (Corex) and phase separation is carried out by centrifugation at 5000 rpm for 5 minutes in a table top Eppendorf centrifuge. The upper phase, containing the nucleic acid, is collected and precipitated by layering with 2 volumes of 95% ethanol. This is followed by spooling of the crude genomic DNA with a sterile glass rod, and resuspension in 40 ml of sterile 15 mM NaCl, 1.5 mM trisodium citrate (0.1×SSC) buffer. RNA is degraded by addition of RNase A solution (2 mg/ml, Pharmacia), to a final concentration of 50 µg/ml and RNase T1 (2500 units/ml, Gibco BRL Life Technologies, Gaithersburg, Md.) to a final concentration of 15 units/ml, to the crude DNA solution and incubating for 3 hours at 37° C. For removal of proteins, 2 ml of SDS (20%) and 2 ml of Proteinase K (5 mg/ml, Gibco BRL) are added and the solution is incubated at 50° C. for 5 minutes followed by 30 minutes at room temperature. The above PCIAA treatment is repeated with a 20 minutes mixing, followed by centrifugation, precipitation of the aqueous layer with ethanol, and spooling of DNA as described above, with the final resuspension in 10 ml of 0.×SSC. The solution can be left overnight at 4° C. at this stage, or processing continued by addition of one ml of 10×SSC (to bring final concentration to 1×SSC), and 10 ml of chloroform-isoamyl alcohol (24:1, v/v, CIAA) with shaking for 15 minutes. The solution is then aliquoted into glass tubes and centrifuged at 5000 rpm for 5 minutes for phase separation. The lower organic phase is removed and the aqueous phase with the interface is re-extracted as described above with CIAA until there is minimal protein at the interface. This is followed by removal of the aqueous layer, precipitation with ethanol, and DNA spooling as described previously. The DNA is resuspended in 5 ml of 0.01×SSC and can be stored overnight. The DNA is dialyzed with one buffer change against 0.01×SSC at 4° C. over a period of 4 hours, repeated once overnight, and then repeated once again for a further 4 hours. The amount of purified genomic DNA is determined by UV spectrophotometry and then sonicated (Branson, model 250/450) for 10 minutes to reduce the size of DNA to less than or equal to 1000 base pairs (bp).
3. Preparation of Enterococcal Crude Lysates Enterococcal isolates for crude lysates are grown overnight at 37° C. on blood TSA plates and cells are collected with a 1 µl plastic loop (PML Microbiological, Richmond, BC, Canada). Cells (equivalent to ≡5×McFarland No. 4 or $3 \times 10^8$ cells/50 µl) are resuspended in 50 µl of lysis buffer composed of 0.05% Triton X-100 and 20 mM TES, pH 6.8. As an alternative, cells are resuspended in 2 ml of lysis buffer and then adjusted to standard McFarland no. 4 (equivalent to ≡$6 \times 10^7$ cells/50 µl). A combination of lytic enzymes, achromopeptidase (Wako Bioproducts, Richmond, Va.) and mutanolysin (ICN Biomedicals, Aurora, Ohio), were added to a final concentration of 150 units/ml and 50 units/ml, respectively. Samples are mixed and incubated at 54–58° C. for 20–30 minutes.

Example 3

Preparation of Thermostable RNASE H

The following example describes one suitable method for preparing thermostable RNase H from *Thermus thermophilus*.

The cloning of the thermostable gene and its expression is described in detail in WO 95/05480 and Bekkaoui et al., *BioTechniques* 20:240–248, 1996 based on the modification of the method by Kanaya & Itaya, *J. Biol. Chem.* 267:10184–10192, 1992. Briefly, the *T. thermophilus* RNase H gene (Kanaya & Itaya, supra) is cloned by PCR into vector pT7-7 (pIDB9) and is subcloned into the vector pET11 (Novagen) resulting in the plasmid pIDB33. Plasmid pIDB33 is subsequently transformed into the bacterial strain BL21(DE3) (Novagen, Madison, Wis.). BL21(DE3) cells containing pIDB33 are grown at 37° C. in LB medium (Sambrook et al, 1990) containing 0.1 mg/ml ampicillin. When the culture is at an $OD_{600}$ of 0.6–0.8, IPTG is added to a final concentration of 0.5 mM and the cells are cultured for four more hours. RNase H is expressed in the inclusion bodies with the pIDB33 construct.

Cells are harvested by centrifugation at 3000×g for 15 minutes at 4° C. Cell pellets are resuspended at 1 g fresh weight in 5 ml of TE buffer (10 mM Tris, pH 7.4, 1 mM EDTA buffer). The cells are lysed on dry ice/ethanol bath using a sonicator (Branson, model 450) and centrifuged at 15,000×g for 30 minutes at 4° C. The pellet is resuspended in 7 M urea in TE buffer, pH 8.0 and incubated with stirring for 2 hours at 40 C. The resuspended cells are sonicated for 2 minutes on ice, followed by centrifugation at 12,000×g for 10 minutes and the supernatant is collected and dialyzed overnight against 1 l of urea sodium acetate buffer (8 M urea, 20 mM sodium acetate, pH 5.5) with two changes. After a centrifugation for 20 minutes at 31,000×g, the clear protein supernatant solution (150 ml) is collected and mixed with approximately 25 ml of pre-swollen phosphocellulose (equilibrated 2× in column buffer, P11, Whatman International Ltd., Kent, UK) for 3 hours. The resulting slurry is washed twice with the urea sodium acetate buffer and poured into a column. The column is connected to an FPLC system (Pharmacia) and step washed twice with 140 mM and 210 mM NaCl in the urea sodium acetate buffer. The protein is then eluted using a 0.21 to 0.7 M NaCl linear gradient in the urea sodium acetate buffer. At the end of the salt gradient, the column is maintained at 0.7 M NaCl until all the protein is eluted. Fractions are analyzed by SDS-PAGE and those containing RNase H are pooled and desalted using a Sephadex G-25 column with buffer containing 150 mM NaCl in 20 mM sodium acetate, pH 5.5. The eluted protein fractions are pooled, concentrated with a Centriprep 10 filter (Amicon, Beverly, Mass.), and stored at –20° C. in glycerol storage buffer (40% glycerol, 150 mM NaCl and 20 mM sodium acetate, pH 5.5).

Example 4

Cycling Probe Reactions

Cycling probe technology (CPT) reaction and conditions are modified from a previously published method (WO 95/14106; Bekkaoui et al., *BioTechniques* 20(2): 240–248, 1996). The chimeric probe is 5' labeled with radioactive [$^{32}$P]-ATP (Sambrook et al., 1990) using T4 polynucleotide kinase (RTG; Pharmacia Biotech, Piscataway, N.J.). Unless otherwise specified, the labeled probe is purified from unincorporated [$^{32}$P]-ATP by G50 NICK column (Pharmacia) chromatography. 1000 cpm of labeled probe corresponds to 0.3 fmol of probe. Unless otherwise specified, the final cycling reaction mixture contains specified concentrations of chimeric probe, and synthetic or natural nucleic acid target, and specified concentration of spermine and EGTA as additives in N-tris[Hydroxymethyl]methyl-2-aminoethanesulfonic acid (TES, Sigma Chemical Co.) based cycling buffer (TES-CB) which has the following composition: 0.05% Triton X-100®, specified concentration of $MgCl_2$, 20 mM TES buffer, pH 6.8. Sample preparations, probes and targets compositions and concentrations, RNase H, test additives, heterologous DNA concentrations, and other assay details are described specifically in the following examples.

Unless otherwise specified, the CPT reactions are incubated for 30 minutes at specified temperature and then stopped by addition of urea loading buffer (10 M urea, 100 mM EDTA and 0.025% each of blue bromophenol and xylene cyanol) on ice. The reaction mixtures are then resolved by 7 M urea- 20% to 24% acrylamide/bisacrylamide (19:1) gel electrophoresis (SDS-PAGE) at 500 Volts, with water cooling. The gel is analyzed on a PhosphorImager™ utilizing IMAGEQUANT™ software (Molecular Dynamics, Sunnyvale, Calif.). The amount of cycled probe is estimated by integration of the areas of bands corresponding to intact and cleaved probe.

Unless otherwise stated, in a CPT reaction Percent Probe Cut is the total amount of cut probe relative to the total amount of the input probe (Equation No. 1).

$$\text{Percent Probe Cut} = (\text{Probe Cut/Total input probe}) \times 100 \quad (1)$$

In a simple CPT system, the C1 background refers to the Percent Probe Cut in the reaction buffer without RNase H or homologous target present. C2 refers to Percent Probe Cut in the presence of RNase H but without homologous target (Equation No. 2).

$$C2 = (\text{Probe cut/Total input probe}) \times 100 \quad (2)$$

For complex CPT system, C3 refers to Percent Probe Cut in the sample (biological samples that contains extraneous components, such as heterologous DNA or proteins) in the absence of RNase H. C4 refers to Percent Probe Cut in the biological sample in the presence of RNase H, but in the absence of homologous target (Equation No. 3).

$$C4 = (\text{Probe cut/Total input probe}) \times 100 \quad (3)$$

Net Percent Probe Cut is the percent of probe cut due to homologous target and is calculated by subtracting the background C2 (simple system),or C4 (complex system) from the Percent Cut (Equations No. 4 or 5, respectively).

$$\text{Net Percent Cut} = \text{Percent Cut} - C2 \quad (4)$$

$$\text{Net Percent Cut} = \text{Percent Cut} - C4 \quad (5)$$

Signal to noise ratio (S:N) for CPT is defined as the ratio of the Percent Probe Cut in the presence of the homologous target to the C2 (simple system, Equation No. 6) or C4 (complex system, Equation No. 7).

$$S:N = \text{Percent Cut}/C2 \quad (6)$$

$$S:N = \text{Percent Cut}/C4 \quad (7)$$

Example 5

Detection of Synthetic VRE Target by CPT Reaction

The following example examines the effectiveness of vanA and vanB chimeric probes for the detection of the synthetic vanA and vanB target by CPT reaction, in a clean system.

In particular, five chimeric probes were designed and tested in CPT reaction for non-specific cleavage both in the absence of the homologous target and RNase H (C 1), and in presence of RNase H and absence of the target (C2). The VRE chimeric probes and targets (specified in Table 1) were synthesized as described in Example 1 and the probes labeled as described in Example 4. Purified *T. thermophilus* RNase H was produced as described in Example 3. The CPT reactions and analysis were carried out essentially as described in Example 4 except for the following: 0.3 fmol specified chimeric probe, $1\times10^{-4}$ pmol specified target, 0.1 µg RNase H, 4 mM $MgCl_2$, in a final reaction volume of 10 µl in TES-CB and a reaction temperature of 65° C.

The results of testing the probes at target concentration of $10^{-4}$ pmol in a simple system are presented in Table 1. These preliminary results show that the specified vanA or vanB chimeric probes result in Net Percent Probe Cut ranging from 61% to 91% and therefore can be used for detecting their complementary synthetic targets.

TABLE 1

Examination of specific and non-specific cleavage of VRE probes in a simple CPT system

| Probe | Target | Background (%) C1 | C2 | Net Probe Cut (%) |
|---|---|---|---|---|
| vanA811L-27 (SEQ ID NO:1) | vanA811L-27T (SEQ ID NO:2) | 2 | 3 | 91 |
| vanB467-27 (SEQ ID NO:3) | vanB467-27T (SEQ ID NO:4) | 2 | 6 | 91 |
| vanB242-27 (SEQ ID NO:5) | vanB242-27T (SEQ ID NO:6) | 5 | 14 | 98 |
| vanB2242-27 (SEQ ID NO:9) | vanB2242-27T (SEQ ID NO:10) | 14 | 6 | 61 |
| vanB857-20 (SEQ ID NO:7) | vanB857-20T (SEQ ID NO:8) | 1 | 4 | 69 |

The above example demonstrated that the designed chimeric vanA and vanB probes can detect their respective complementary synthetic targets in a simple CPT system.

Example 6

Detection of VRE by CPT Reaction Using Genomic DNA

The following example demonstrates that the additives spermine and EGTA improve the detection of VRE in CPT reaction using purified genomic DNA.

In this experiment two chimeric probes were tested for detection of the vanA and vanB genes in VRE. The effects of the presence or absence of spermine and EGTA were examined in the CPT reaction for the detection of vanA gene. For vanB detection only the effect of spermine and EGTA in the CPT reaction was examined. The VRE chimeric probes (specified in Table 2) were synthesized as described in Example 1 and labeled as described in Example 4. The genomic DNA was prepared from the VanA VRE isolate (from Mt. Sinai Hospital), the VanB *E. faecalis* (ATCC No. 51299) and the VSE, *E. faecalis* (ATCC No. 29212) described in Example 2. The purified *T. thermophilus* RNase H was produced as described in Example 3. The CPT reaction and analysis were carried out as described in Example 4 except for the following: 0.9 fmol of specified chimeric probe, 100–150 ng of genomic DNA, 1 µg RNase H, 4.0 mM $MgCl_2$, with or without 0.5 mM spermine, 1.0 mM EGTA, in TES-CB to a total volume of 30 µl.

Table 2 summarizes the results of the above experiment. For detecting the vanA gene, it was observed that in the absence of spermine and EGTA, the C4 background was greater and the signal to noise ratio was less than 2. This was in contrast to the CPT reaction containing the additives, spermine and EGTA, where the signal to noise ratio increased to approximately 5. The presence of spermine and EGTA in the CPT reaction for detection of vanB gene, resulted in signal to noise ratio of approximately 3. Therefore the presence of spermine and EGTA improves the CPT reaction, allowing for the detection of both vanA and vanB genes of VRE. It should be noted that due to limited number of experiments carried out using genomic DNA, the above additive concentrations have not been optimized for all the probes in the genomic system.

TABLE 2

Effect of spermine and EGTA on the signal to noise ratios for the detection of vanA and van B genes from genomic DNA using the vanA and vanB chimeric probes in CPT reactions.

| Probe | Additives | C4[2] Background (%) | VRE Probe Cut (%) | S:N[1] |
|---|---|---|---|---|
| vanA811L-27 (SEQ ID NO:1) | None | 30 | 55 | 1.8 |
| vanA811L-27 | SP + EGTA | 7 | 34 | 4.9 |
| vanB242-27 (SEQ ID NO:5) | None | ND[4] | ND[4] | — |
| vanB242-27 | SP + EGTA | 20 | 62 | 3.1 |

[1]S:N refers to signal to noise ratio
[2]C4 background refers to Percent Probe Cut in the presence of VSE
[3]SP refers to spermine
[4]ND refers to not done The above experiment demonstrates the utility of spermine and EGTA in CPT reaction for the detection of the vanA and vanB genes of VRE using purified genomic DNA.

Example 7

Conditions in CPT Reaction for Detection of VRE in Crude Lysates

The following example summarizes the conditions for the VRE chimeric probes for detection of the vanA, vanB and vanB2 genes of VRE from crude lysates using the CPT reaction.

Preliminary optimization experiments for the concentrations of spermine and EGTA, and temperature to be used in the CPT reaction containing crude lysates were carried out. The concentrations of spermine and EGTA tested were between 0.5 mM to 2.0 mM. For each probe or set of probes a temperature profile study was carried out by examining CPT reaction from approximately 55° C. to 65° C. using 2° C. incremental steps. The optimal conditions were chosen based on the best discrimination between VRE and VSE; and these conditions are summarized in Table 3.

TABLE 3

Concentrations of spermine and EGTA, and temperature of cycling for the VRE chimeric probes used with crude lysates.

| Probe(s) | Spermine | EGTA | Temperature |
|---|---|---|---|
| vanA811L-27 (SEQ ID NO:1) | 0.75 mM | 1.0 mM | 63° C. |
| vanB467-27 (SEQ ID NO:3) | 1.0 mM | 1.0 mM | 59° C. |
| vanB242-27 (SEQ ID NO:5) | 2.0 mM | 1.5 mM | 63° C. |
| vanB242-27 and vanB2242-27 (SEQ ID NOS:5 & 9) | 2.0 mM | 1.5 mM | 63° C. |
| vanA811L-27 and vanB857-20 (SEQ ID NOs:1 & 7) | 0.95 mM | 4.0 mM | 63° C. |

TABLE 4

Use of vanA, vanB and vanB2 chimeric probes for CPT detection of homologous target in VRE from crude lysates using spermine and EGTA in the reaction.

| Probe | Additives | C4[1] Background (%) | VRE Probe Cut (%) | S:N[2] |
|---|---|---|---|---|
| vanA811L-27 (SEQ ID NO:1) | None | 82 | 82 | 1 |
| vanA811L-27 | SP + EGTA | 5 | 56 | 11 |
| vanB467-27 (SEQ ID NO:3) | SP + EGTA | 5 | 56 | 11 |
| vanB242-27 (SEQ ID NO:5) | SP + EGTA | 19 | 63 | 3 |
| vanB2242-27 (SEQ ID NO:9) | SP + EGTA | 20 | 8 1 | 4 |
| vanB857-20 (SEQ ID NO:7) | SP + EGTA | 6 | 57 | 9 |

[1]C4 background refers to Percent Probe Cut in the presence of VSE
[2]S:N refers to signal to noise ratio, i.e., VRE Probe Cut/C4
[3]SP refers to spermine

Example 8

Detection of VRE Genes in Crude Lysates by CPT Reactions

The following example demonstrates that the VRE chimeric probes optimized in Example 7 can be used for detecting the vanA, the vanB and the vanB2 genes from crude bacterial lysates using the CPT reaction.

The following experiment was designed to examine the effect of spermine and EGTA in CPT reactions using crude lysates of VRE or VSE. The vanA probe was tested both in the presence and absence of spermine and EGTA, and for the remaining probes, only the effect of combined spermine and EGTA in crude lysates was examined (Table 4).

The five chimeric probes used for detection of the vanA, vanB and vanB2 genes of VRE are specified in Table 4. These probes were synthesized as described in Example 1 and labeled as described in Example 4. Purified *T. thermophilus* RNase H was produced as described in Example 3. The crude lysates were prepared from the VanA *E. faecalis* VRE isolate (IDB No. 339 obtained from Mt. Sinai Hospital), the VanB *E. faecalis* (ATCC No. 51299) and the VSE, *E. faecalis* (ATCC No. 29212). VRE and VSE cells were resuspended to McFarland No. 4 standard and lysed as described in Example 2. Prior to the reaction, crude lysates were heat denatured (95° C. for 5 minutes) and then transferred to a waterbath set at a temperature optimal for each CPT probe. The CPT reaction and analysis were carried out as described in Example 4 except for the following: 1.8 fmol of specified chimeric probe (Table 4), 50 μl of VRE or VSE crude lysates, 3.3 μg RNase H, and 2 mM MgCl$_2$ in TES-CB to a final reaction volume of 100 μl. For each of the probes the specified spermine and EGTA conditions are shown in Example 7, Table 3.

Table 4 summarizes the results of detecting VRE in crude lysates using the five specific chimeric probes in CPT reaction with the additives spermine and EGTA. Briefly, in the absence of spermine and EGTA, vanA811L-27 probe could not detect the vanA gene in crude lysates due to the high C4 background. However, upon addition of spermine and EGTA to the reaction, the C4 was reduced allowing for successful detection of the vanA gene. Presence of spermine and EGTA in reaction mixtures of the vanB and vanB2 probes allowed for the successful detection of the respective targets.

The above example demonstrates the utility of the chimeric vanA, vanB and vanB2 probes in CPT for the detection of the vanA, vanB and vanB2 genes using crude lysates of the enterococcal isolates.

Example 9

Screening of Enterococcal Isolates for VANA and VANB Genes by CPT Reactions Using Specific Chimeric Probes in Crude Lysates The following example demonstrates the use of CPT reaction for screening enterococcal isolates for the detection of the vanA and vanB genes.

The first experiment was designed to test the vanA811L-27 (SEQ ID NO:1) chimeric probe for the detection of the vanA gene from 440 isolates of enterococci. The second experiment was designed to test vanB467-27 (SEQ ID NO:3) for screening of VRE isolates for the vanB gene from a total of 440 isolates. In these experiments the chimeric probes were synthesized as described in Example 1 and labeled as described in Example 4. Purified *T. thermophilus* RNase H was produced as described in Example 3. VRE and VSE cells were resuspended to 5xMcFarland No. 4 standard cell density and lysed as described in Example 2. Prior to the reaction, crude lysates were heat denatured (95° C. for 5 minutes) and then transferred to a waterbath set at temperature optimal for each CPT probe. The CPT reaction and analysis were carried out as described in Example 4 except for the following: 1.8 fmol of specified chimeric probe, 50 μl of VRE or VSE crude lysates, 3.3 μg RNase H, and 2 mM MgCl$_2$, in TES-CB to a final reaction volume of 100 μl. For the vanA CPT assay, TES-CB contained 0.75 mM spermine and 1 mM EGTA and reactions were carried out at 63° C.; for the vanB CPT assay, TES-CB contained 1 mM spermine and 1 mM EGTA and reactions were carried out at 59° C.

Figure 2:
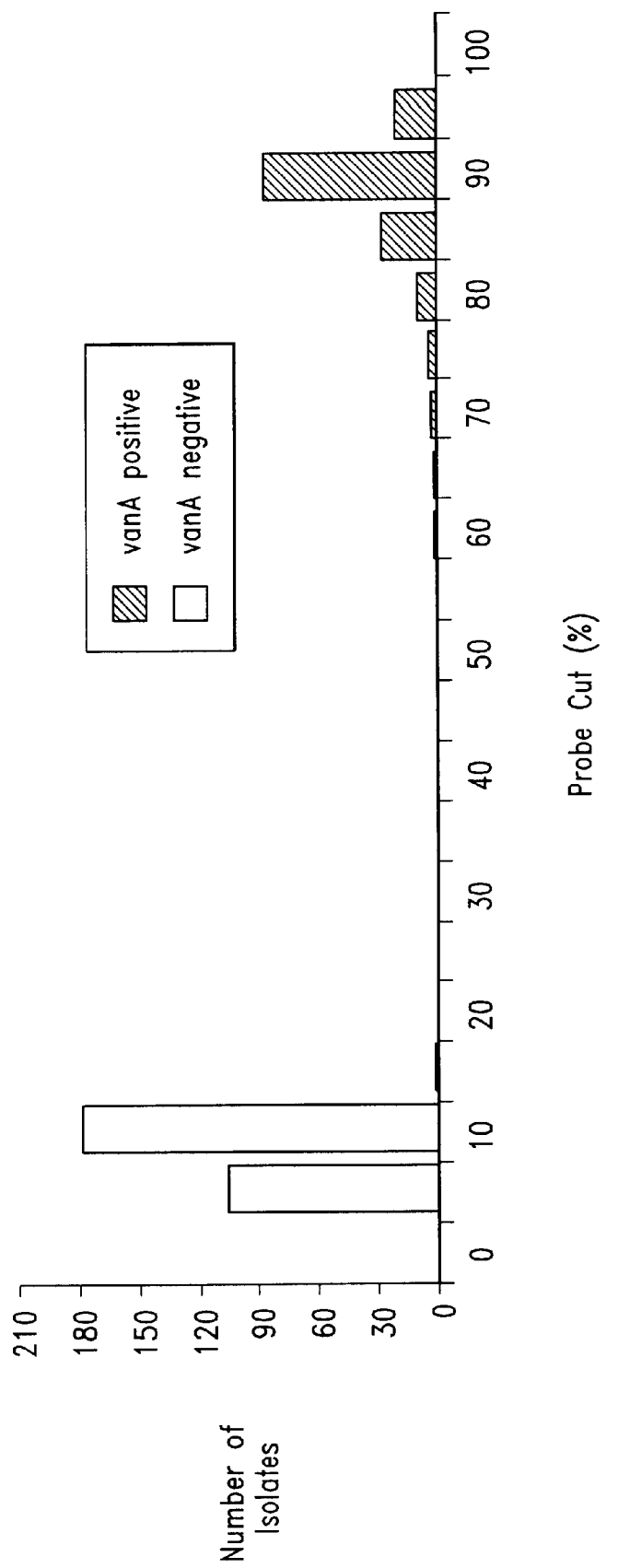
FIG. 2 is a histogram showing the frequency distribution results of screening 440 enterococcal isolates for the vanA gene from crude lysates using CPT reaction. The $^{32}$P-labeled chimeric probe was vanA811L-27 (SEQ ID NO:1) and the reaction mixture contained the combination of 0.75 mM spermine and 1.0 mM ethylenebis(oxyethylenitrilo)-tetracetic acid (EGTA). The isolates could easily be divided into two populations corresponding to vanA positive and vanA negative enterococci based on the Probe Cut (%).

FIG. 2 depicts the results of the vanA screen test of the 440 isolates of VRE and VSE by CPT reaction using the vanA811L-27 chimeric probe. Briefly, the vanA chimeric probe correctly identified all 154 VanA isolates as vanA positives. All of the remaining isolates were grouped together as vanA negatives. These values allowed for the differentiation of the vanA positives (i.e., VanA) from the vanA negatives (i.e., VanB, VanC VRE and VSE) with a signal to noise ration of ≡14. The low probe cleavage in the vanA negative isolates demonstrated that the vanA811L-27 did not cross-react with either vanB or vanC genes.

Figure 3:
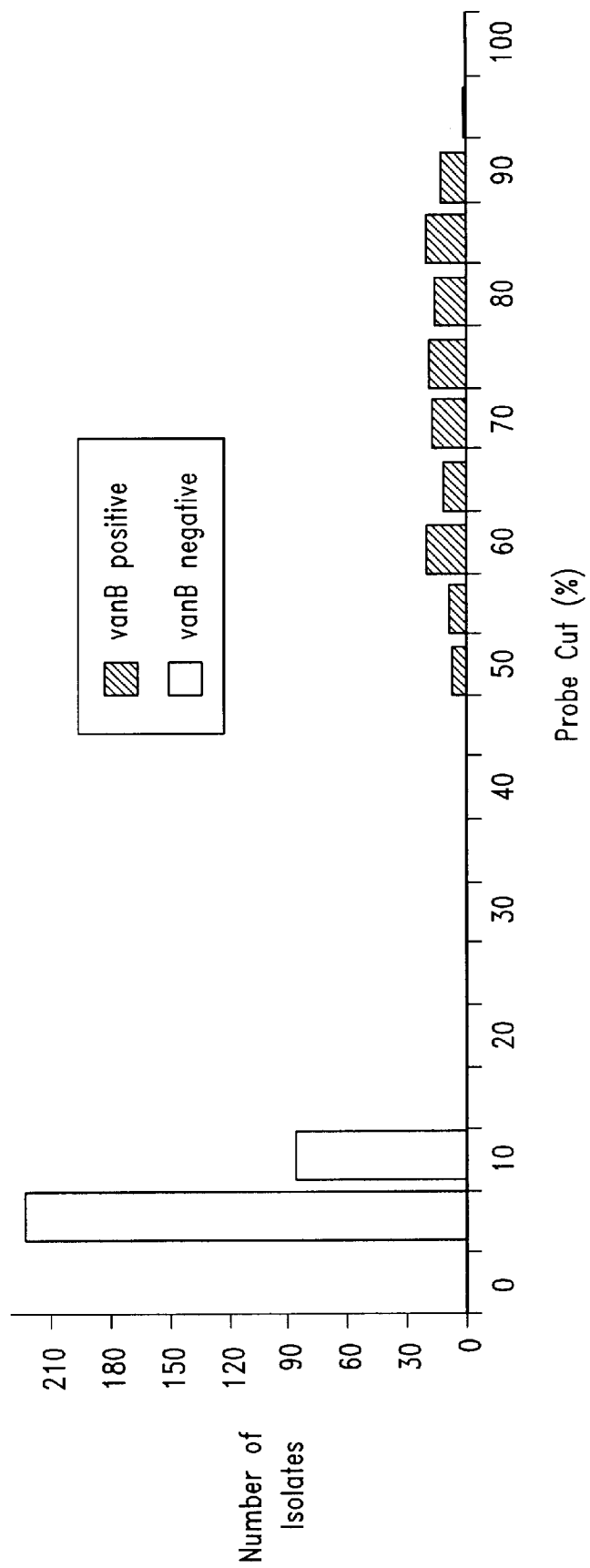
FIG. 3 is a histogram showing the frequency distribution results of screening 440 enterococcal isolates for the vanB gene from crude lysates using CPT reaction. The $^{32}$p labeled chimeric probe was vanB467–27 (SEQ ID NO:3) and the reaction mixture contained the combination of 1.0 mM spermine and 1.0 mM EGTA. The isolates could easily be divided into two populations corresponding to vanB positive and vanB negative enterococci based on the Probe Cut (%).

FIG. 3 depicts the results of the vanB screen testing of 440 isolates of VRE and VSE for the vanB gene by CPT reaction using the vanB467-27 chimeric probe. The vanB chimeric probe correctly identified all of the 131 VanB isolates as vanB positives (FIG. 3). The remaining isolates were vanB negative and formed a discrete group (FIG. 3). These values allowed for the differentiation of the vanB positives from the vanB negatives (i.e., VanA, VanC and VSE) with a signal to noise ratio of ≡14. The low probe cleavage in the vanB negative isolates demonstrated that the vanB467-27 chimeric probe did not cross-react with the vanA or vanC genes.

The above example demonstrates a successful screening of the vanA and vanB genes of VRE clinical isolates by CPT reactions using chimeric probes vanA81IL-27 (SEQ ID NO:1) and vanB467-27 (SEQ ID NO:3), respectively.

Example 10

Multiplex CPT Detection of VANA and VANB VRE Isolates

The following example demonstrates the simultaneous use of vanA and vanB chimeric probes for detecting the vanA and vanB genes from VRE.

This experiment was designed to test the use of two chimeric probes, vanA811L-27 (SEQ ID NO:1) and vanB857-20 (SEQ ID NO:7), in a single CPT reaction for differentiating between the VRE (VanA and VanB) and VSE isolates.

In this experiments the chimeric probes were synthesized as described in Example 1 and labeled as described in Example 4. Purified *T. thermophilus* RNase H was produced as described in Example 3. VRE and VSE cells were resuspended to 5×McFarland No. 4 standard and lysed as described in Example 2. Prior to the reaction, crude lysates were heat denatured (95° C. for 5 minutes) and then transferred to a waterbath set at a temperature optimal for CPT reaction. The CPT reaction and analysis were carried out as described in Example 4 except for the following: 1.8 fmol of each chimeric probe, 50 µl VRE or VSE crude lysates, 3.3 µg RNase H, 2 mM MgCl$_2$, 0.95 mM spermine and 4 mM EGTA, in TES-CB to a final reaction volume of 100 µl. Cycling was carried out at 63° C.

Figure 4:
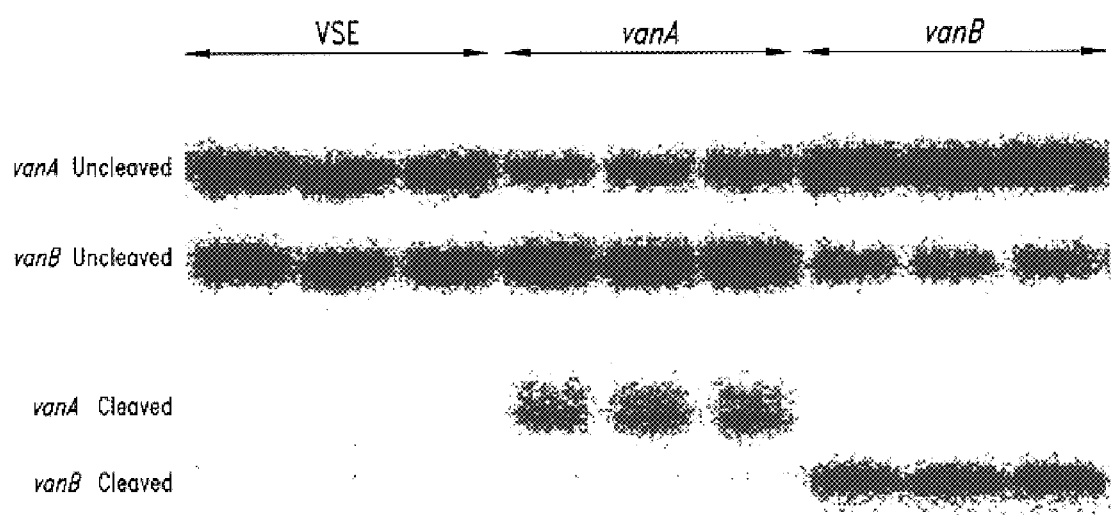
FIG. 4 depicts the results of gel electrophoresis from the experiment examining simultaneous use of vanA and vanB chimeric probes (SEQ ID NOs. 2 and 7) for detection of the vanA or the vanB gene in VRE by multiplexing cycling probe reaction.

FIG. 4 depicts the gel electrophoresis of the CPT products and the results from the experiment examining the use of both vanA and vanB chimeric probes for detecting the vanA and vanB VRE simultaneously. Table 5 summarizes the results from the above experiment. Briefly, VSE isolates showed minimal probe cleavage. VRE isolates identified as VanA type showed cleavage of vanA811L-27 probe (47%) while vanB467-27 probe remained uncleaved. In contrast, the vanB857-20 probe was cleaved (57%) in isolates identified as VanB. Both vanA and vanB assays resulted in differentiation of VRE from VSE with signal to noise ratio of 9 and 8, respectively.

TABLE 5

The results of simultaneous use of two chimeric probes for detecting vanA and vanB genes from VRE by Multiplex CPT.

| Probe | C4[1] Background (%) | VRE gene Isolate | VRE Probe Cut (%) | S:N[2] |
|---|---|---|---|---|
| vanA811L-27 | 5 | vanA | 47 | 9.4 |
| (SEQ ID NO:1) | | vanB | 8 | 1.6 |
| vanB857-20 | 7 | vanB | 57 | 8.1 |
| (SEQ ID NO:7) | | vanA | 6 | 0.9 |

[1]C4 background refers to Percent Probe Cut in the presence of VSE
[2]S:N refers to signal to noise ratio, i.e., VRE Percent Probe Cut /C4

The above example demonstrates that both the vanA and vanB genes from VRE can be detected and differentiated using multiplex CPT.

Example 11

Non-isotopic VRE Assays Using Single or Dual Probes

Figure 5:
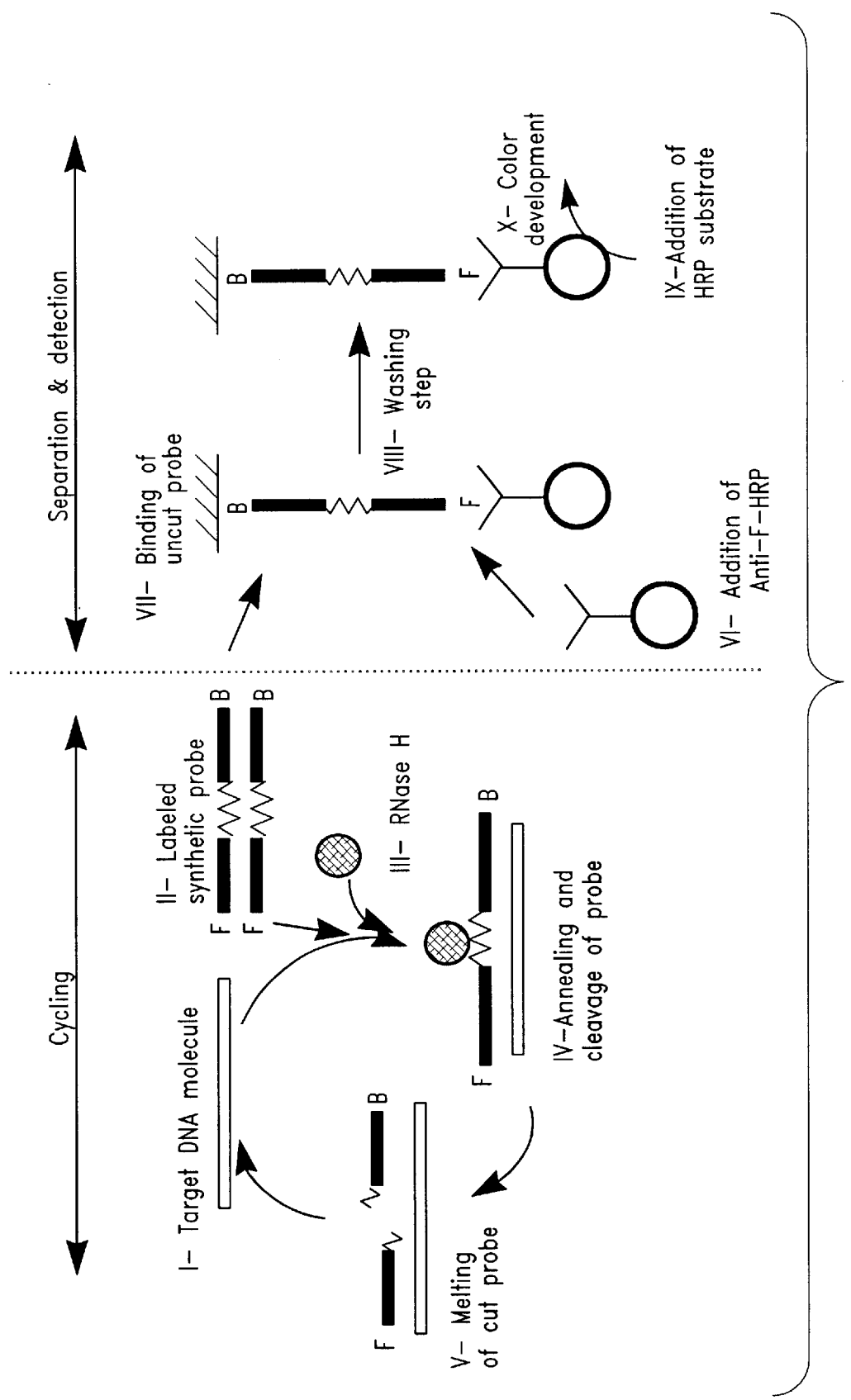
FIG. 5 is a schematic illustration of the one embodiment of a non-isotopic cycling probe reaction. Briefly, single-stranded target (I) serves as a catalyst for CPT. In the presence of a fluoresceinated (F) and Biotinylated (B) DNA-RNA-DNA chimeric probe (F-DNA-RNA-DNA-B) (II) and RNase H (III), the RNA portion of the probe-target complex (IV) is cleaved by RNase H. The shorter cleaved probe fragments dissociate from the target thereby regenerating the target DNA for further cycling (V). The anti-fluorescein antibody coupled to horse radish peroxidase (anti-F-HRP) is added (VI) and the reaction is transferred to streptavidin coated plates. The uncut probe bound to anti-F-HRP is captured using the plates (VII). Excess antibody is washed away (VI) and the HRP substrate is added (IX) to measure the amount of uncleaved probe. The absorbance, or color development (X), is inversely proportional to the amount of target DNA.

The non-isotopic VRE assay which combines PCT with an enzyme immunoassay (CPT-EIA) is schematically illustrated in FIG. 5. This assay utilizes a DNA-RNA-DNA chimeric probe providing an RNase H sensitive scissile linkage when bound to the complementary base sequences of the vanA or vanB gene. Uncleaved probe is detected by binding of the probe to a solid surface and attachment of an antibody conjugated with horse radish peroxidase, which converts a substrate to a colored end product. Cleavage of the probe (vanA or vanB positive) prevents binding of the probe-antibody complex to the solid surface thus preventing formation of the colored end product.

The following example describes generally rapid single and dual probe non-isotopic CPT-EIA assay for the detection of VRE from crude lysates. The lysis method has been developed and optimized for VRE and VSE.

The single or dual chimeric probes specific for detecting vanA, vanB or vanB2 are synthesized, fluoresceinated and biotinylated as described in Example 1. The purified thermostable RNase H is prepared as described in Example 3. The sources of enterococcal isolates and growth conditions are as described in Example 2.

A. Lysis Step

The cells are lysed by placing 1 µL loopful of culture growth in 100 µL of Lysis Reagent. The composition of the Lysis Reagent is as follows: 0.2 mg/ml lysozyme (Sigma), 0.025 mg /ml mutanolysin (ICN Biomedicals, Aurora, Ohio)), 0.05% (v/v) Triton X$_{100}$® and 20 mM TES buffer, pH 6.8. The samples are incubated at 54° C. for 15 minutes after which 10 µl of SDS, Clarifying Reagent, is added to a final concentration of 0.07%. Samples are mixed and incubated at room temperature for 5 minutes. For dual probe assay the lysate sample is split into two 50 µl aliquots at this point.

B. Cycling Conditions

The Cycle reagents for single and dual assays are as follows: 50 µl crude lysate, 1.0% Triton X-100®, 2 mM MgCl$_2$, 25 µM EDTA pH 8.0, 0.625 µM spermine, 0 to 3% ethanol, lyophilization additives (100 mM trehalose, 20 ppm Proclin, 0.1% PVP, 2 to 5 µg/µl BSA) in 20 mM TES, pH 7.6. The DNA from the crude lysates is denatured at 95° C. for 5 minutes and than transfered to 540 C dry bath prior to carrying out the CPT reaction. In the following examples, the type and concentration of probe(s) and concentration of thermostable RNase H are specified. 50 µl is then added to each sample in a final reaction volume of 160 µl for single probe and 110 µl for dual probe, and CPT is carried out at 54° C. for 30 min.

C. Detection

After cycling, 100 µL of Binding Reagent (Peroxidase Stabilizing Buffer, DAKO, Mississauga, ON) containing dilution of sheep polyclonal anti-fluorescein-horse radish peroxidase conjugated antibody is added to the tubes. The CPT reaction volume is transferred to streptavidin coated wells (Boehringer Mannheim GmbH, Germany), and incubated for 10 minutes at room temperature. The liquid is discarded and the plate is washed twice with 300 µl of Wash Buffer (137 mM NaCl, 2.7 mM KCl, 1.8 mM KH$_2$PO$_4$, 10.1 mM Na$_2$HPO$_4$, 0.5% Tween 20, pH of 7.3). This is followed by addition of 200 µl of substrate (Tetramethylbenzidine/ H$_2$O$_2$, Bio-Rad) and allowed to develop for 5 minutes at room temperature. The development is stopped by using 100 µl of Detection Stop Reagent (750 mM Tris, 1.5% (w/v) sodium dodecyl sulfate, pH of 7.7). The plate is read using a Vmax plate reader set at OD$_{650nm}$.

Example 12

Non-isotopic VRE Assay Using Dual Probes

This example describes a rapid two probe non-isotopic CPT assay for the detection of VRE from crude lysates.

A large scale screen for identifying the vanA or vanB genes from 440 enterococcal isolates was carried out using the non-isotopic CPT-EIA VRE assay with the specific chimeric probes for vanA, vanA812L-25 (SEQ ID NO:12), and vanB vanB467-27 (SEQ ID NO:3). All 440 isolates were previously characterized by conventional susceptibility methods and used for screening with radioactive CPT assays. Thus, the collection of isolates included previously characterized 111 VSE, 154 VanA, 131 VanB, and 44 VanC. The dual probe assay and analysis was carried out as described in Example 12 with 5 fmol of vanA811L-27 and 5 fmol of vanB467-27 probe and 1.64 µg RNase H per reaction.

Figure 6:
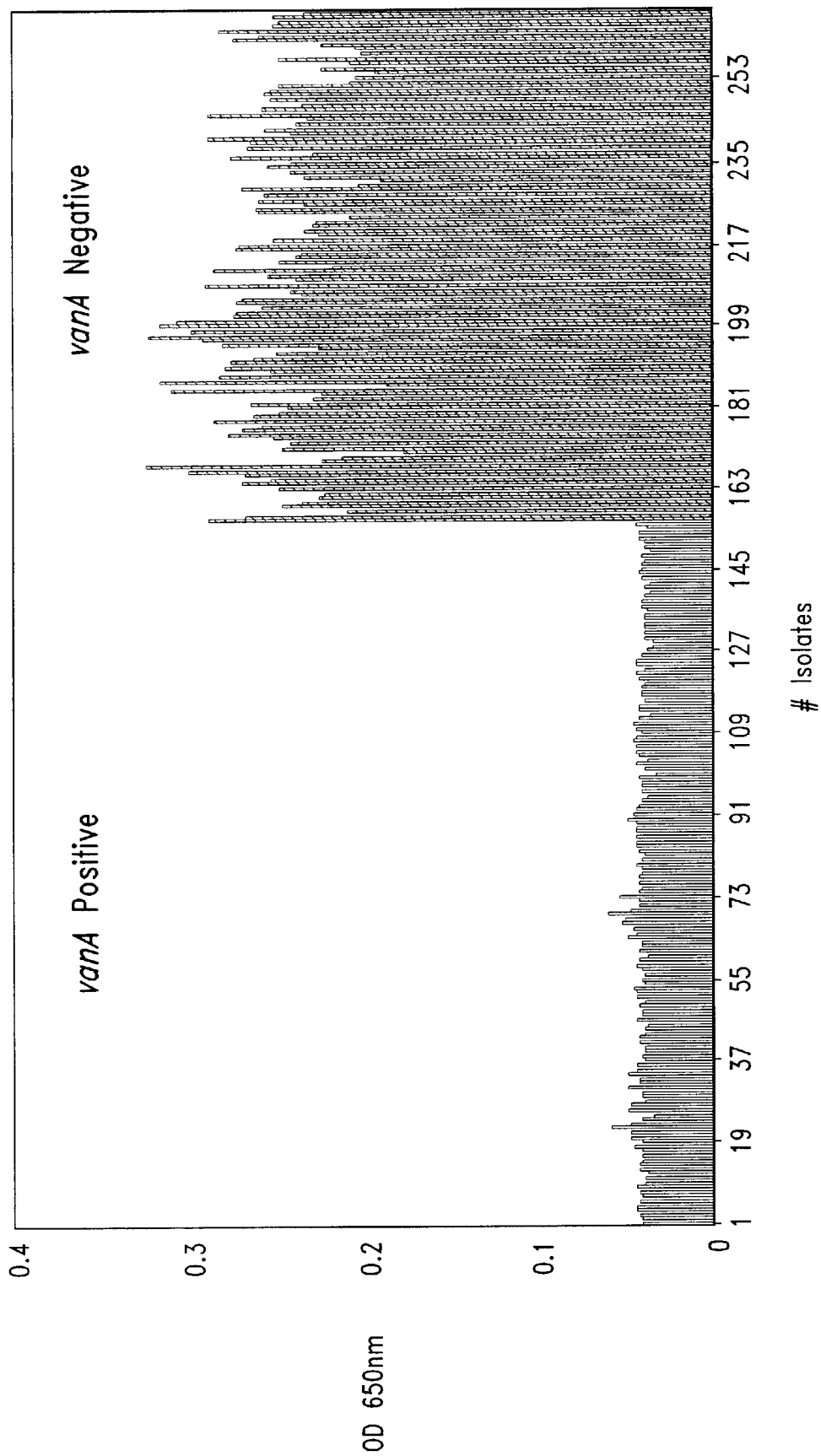
FIG. 6 is a histogram showing the frequency distribution results of screening 440 enterococcal isolates for the vanA gene from crude lysates using the chimeric probe vanA812L-25 (SEQ ID NO:12) in the non-isotopic CPT assay. The isolates could easily be divided into two populations corresponding to vanA positive and vanA negative enterococci based on the optical density at 650 nm ($OD_{650}$).
Figure 7:
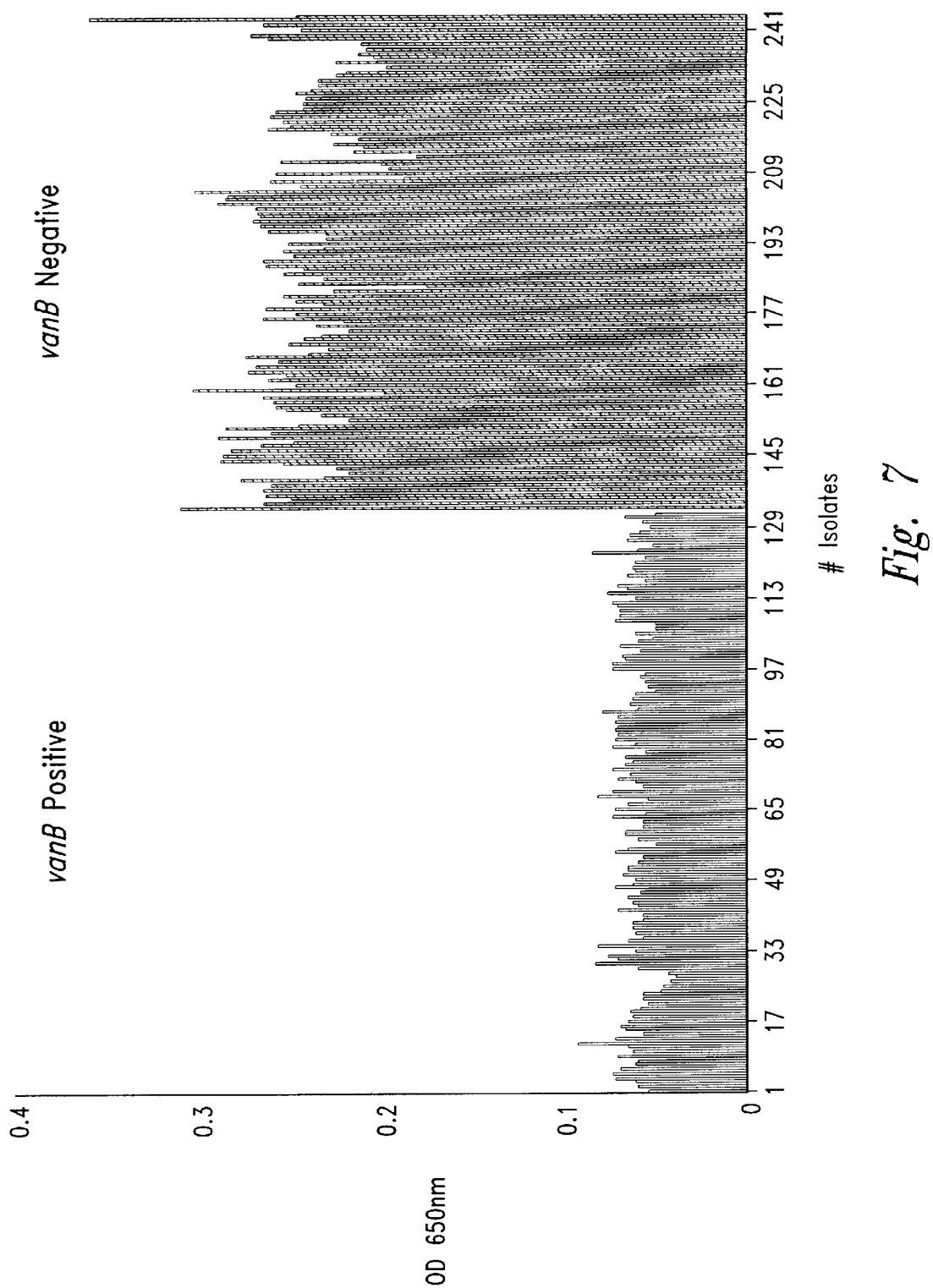
FIG. 7 is a histogram showing the frequency distribution results of screening 440 enterococcal isolates for the vanB gene from crude lysates using the chimeric probe vanB467-27 (SEQ ID NO:3) in the non-isotopic CPT assay. The isolates could easily be divided into two populations corresponding to vanB positive and vanA negative enterococci based on the $OD_{650}$.

FIGS. 6 and 7 summarize the results of the CPT-EIA assay for detecting the vanA an the vanB genes from crude enterococcal isolates. FIG. 6 shows that both the VanA and non-VanA isolates could easily be separated based on their optical densities. All the VanA isolates were observed to have OD values less than 0.1 while the non-VanA isolates had OD values greater than 0.2. Therefore, all of the 154 VanA isolates screened with vanA811L-27 probe were correctly identified as having the vanA gene target sequence. Similarly, FIG. 7 shows that the vanB467-27 probe correctly identified all the 131 VanB isolates from the non-VanB isolates. The OD values for the VanB isolates were observed to be less than 0.1 while the remaining isolates tested which did not contain vanB gene sequence, had OD values greater than 0.2.

The above example successfully demonstrates the use of specific vanA and vanB probes in CPT-EIA assay for detecting the vanA and the vanB genes from VanA or VanB isolates and differentiating them from the non-VanA/B isolates.

Example 13

Non-isotopic VRE Assay Using Single Chimeric Probe

The following example describes a rapid single probe non-isotopic CPT assay for the detection of VRE from crude lysates.

A small scale screen for identifying the vanA and vanB genes from 30 enterococcal isolates was carried out using non-isotopic CPT-EIA-VRE assay with the single chimeric probe vanABmod5-23 (SEQ ID NO:21; IDB No. 476). The isolates were composed of 10 VSE, 10 VanA and 10 VanB and formed the challenge subset of the 440 enteroccal isolates described in Example 2. The assay and analysis was carried out for single probe assay as described in Example 11 using 15 fmol of vanABmod5-23 and 2.0 µg RNase H per reaction.

The experimental results showed that the vanABmod5 probe could easily distinguish the VanA or VanB isolates from the VSE isolates. It was observed that all isolates had OD greater than 0.28 and a mean OD of 0.31 while the OD values for VRE isolates was less than or equal to 0.96. The VanA isolates had a mean OD of 0.071 and VanB isolates had a mean OD of 0.073. Based on these results, the use vanABmod5 probe under the above conditions resulted in good discrimination between VRE and VSE isolates.

The above example successfully demonstrates the use of a single probe CPT-EIA for detecting both the vanA and the vanB genes from the VRE isolates and differentiating them from the VSE isolates.

Example 14

Specificity of the Non-isotopic VRE Assay Using Single Chimeric Probe

The following example examines the single VRE probe for specificity to vanA and vanB genes by testing VRE types other than VanA or VanB and vancomycin resistant bacterial species other than enterococci.

For the VRE, VSE and non-enterococcal panel test the single probe assay was carried out as described in Example 11 with the following changes: (i) in Cycling conditions: 15 fmol vanABmod5-23 probe (SEQ ID NO:21; IDB Seq. No. 476), 2 µg RNase H, (with no lyopholization additives); and (ii) in the Detection step 1/750 dilution of Binding Reagent was used.

The following two tables summarizes the results of the above experiments. The results from Table 6 show that the vanABmod5 probe was found to be specific only for the vanA or vanB gene of the control isolates but not for the VSE or the non-enterococcal isolates examined.

Table 6 shows the results of specificity testing of non-enterococcal species by the non-isotopic VRE assay using a single chimeric probe, vanABmod5-23 (SEQ ID NO:21), designed for detecting vanA or vanB genes.

| Enterococcal and non-enterococcal test isolates | Isolate # | OD$_{650nm}$ |
| --- | --- | --- |
| VSE control | 84 | 0.235 |
| vanA control | 339 | 0.070 |
| vanB control | 326-1 | 0.070 |
| Leuconostoc spp. | 372 | 0.242 |
| Leuconostoc spp. | 373 | 0.251 |
| Aerococcus viridans | 939 | 0.197 |
| Pediococcus pentosaceus | 940 | 0.191 |
| Aerococcus urinae | 941 | 0.235 |
| Leuconostoc mesenteroides | 942 | 0.300 |
| Lectococcus lactis | 943 | 0.199 |

Table 7 shows that the chimeric probe was specific for the vanA or vanB controls and did not cross-react with VanC isolates or the VSE control.

TABLE 7

Shows the results of specificity testing of non-VanA or VanB enterococcal species by the non-isotopic VRE assay using a single chimeric probe, vanABmod5-23 (SEQ ID NO: 21), designed for detecting vanA or vanB genes.

| Enterococcal test isolates | Isolate # | OD$_{650nm}$ |
| --- | --- | --- |
| VSE control | 84 | 0.235 |
| vanA control | 339 | 0.070 |
| vanB control | 326-1 | 0.070 |
| VanC | 804 | 0.275 |
| VanC | 805 | 0.337 |
| VanC | 806 | 0.336 |
| VanC | 807 | 0.347 |
| VanC | 808 | 0.355 |
| VanC | 809 | 0.377 |
| VanC | 811 | 0.396 |
| VanC | 812 | 0.356 |
| VanC | 813 | 0.269 |
| VanC | 814 | 0.390 |

From the above experiment results, the non-isotopic single probe VRE assay using the vanABmod5-23 probe was successfully shown to be specific for the enterococcal vanA or vanB genes and did not cross-react with enterococcal VanC, VSE or other non-enterococcal species tested.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for determining the presence of a vancomycin antibiotic resistant gene of enterococci in a biological sample, comprising:
    (a) lysing cells contained within the biological sample to expose at least one target nucleic acid molecule;
    (b) reacting said target nucleic acid molecule with a scissile-link containing a nucleic acid probe selected from the group consisting of SEQ ID NO:1; SEQ ID NO:3; SEQ ID NO:7; SEQ ID NO:9; SEQ ID NO:16; and SEQ ID NO:17; and with an enzyme molecule under conditions and for a time sufficient for the target and probe to hybridize to form at least one double-stranded, target-probe complex, said enzyme molecule being capable of cleaving said scissile link of said target-probe complex such that one or more fragments of the nucleic acid probe is released from said complex; and
    (c) determining whether cleaved portions of the nucleic acid probe are produced, and thereby detecting the presence of a vancomycin antibiotic resistant gene.

2. The method according to claim 1 wherein the step of determining comprises detecting a decrease in the amount of uncleaved probe.

3. The method according to claim 1 wherein the step of determining comprises detecting an increase in said cleaved portions of the nucleic acid probe.

4. The method according to claim 1 wherein the enzyme molecule comprises RNase H.

5. The method according to claim 1 wherein said target nucleic acid molecule is selected from the group consisting of vanA, vanB, and vanB2.

6. The method according to claim 1 wherein said target nucleic acid molecule comprises vanA.

7. The method according to claim 1 wherein said target nucleic acid molecule comprises vanB.

8. The method according to claim 1 wherein said target nucleic acid molecule comprises vanB2.

9. The method according to claim 1 wherein more than one vancomycin antibiotic resistant gene is detected simultaneously.

10. The method according to claim 1 wherein said detected vancomycin antibiotic resistant gene is vanA, vanB, or vanB2 and not vanC.

11. The method according to claim 1 wherein said biological sample is selected from the group consisting of blood, urine, stool and abscess.

12. The method according to claim 1 wherein said biological sample is first grown on a bacteriologic growth medium.

13. The method according to claim 1 wherein said probe is nucleotide sequence 5'-CCGGaaaaAGGCTCN$^3$GA-3' (SEQ ID NO:16), wherein N$^3$ can be a nucleotide, an abasic nucleotide or a universal nucleotide.

14. The method according to claim 1 wherein said probe is nucleotide sequence 5'-CN$^1$CAN$^2$CCGACCTCacagCCCGAAA-3' (SEQ ID NO:17), wherein N1 and N$^2$ can be a nucleotide, an abasic nucleotide or a universal nucleotide.

15. A kit for detecting the presence of a vancomycin antibiotic resistant gene of enterococci in a biological sample, comprising:
    (a) one or more scissile-link containing nucleic acid probe selected from the group consisting of SEQ ID NO:1; SEQ ID NO:3; SEQ ID NO:7; SEQ ID NO:9; SEQ ID NO:16; and SEQ ID NO:17; and
    (b) an enzyme capable of cleaving said scissile link when said probe is bound to said vancomycin antibiotic resistant gene.

16. The kit according to claim 15 wherein more than one vancomycin antibiotic resistant gene is detected simultaneously.

17. The kit according to claim 15 wherein said enzyme is RNase H.

* * * * *